US011759090B2

(12) United States Patent
Ye et al.

(10) Patent No.: US 11,759,090 B2
(45) Date of Patent: *Sep. 19, 2023

(54) IMAGE-BASED AIRWAY ANALYSIS AND MAPPING

(71) Applicant: Auris Health, Inc., Redwood City, CA (US)

(72) Inventors: Menglong Ye, Mountain View, CA (US); Ritwik Ummalaneni, San Mateo, CA (US)

(73) Assignee: Auris Health, Inc., Redwood City, CA (US)

( * ) Notice: Subject to any disclaimer, the term of this patent is extended or adjusted under 35 U.S.C. 154(b) by 299 days.

This patent is subject to a terminal disclaimer.

(21) Appl. No.: 17/124,182

(22) Filed: Dec. 16, 2020

(65) Prior Publication Data

US 2021/0169589 A1 Jun. 10, 2021

Related U.S. Application Data

(63) Continuation of application No. 16/427,092, filed on May 30, 2019, now Pat. No. 10,898,275.

(Continued)

(51) Int. Cl.
*A61B 1/00* (2006.01)
*A61B 34/20* (2016.01)
(Continued)

(52) U.S. Cl.
CPC .... *A61B 1/00006* (2013.01); *A61B 1/000094* (2022.02); *A61B 1/00097* (2022.02);
(Continued)

(58) Field of Classification Search
CPC .......... A61B 1/00006; A61B 1/000094; A61B 1/00097; A61B 1/00149; A61B 1/2676;
(Continued)

(56) References Cited

U.S. PATENT DOCUMENTS 4,745,908 A 5/1988 Wardle
5,273,025 A 12/1993 Sakiyam et al.
(Continued)

FOREIGN PATENT DOCUMENTS

CN 101147676 3/2008
CN 101147676 A 3/2008
(Continued)

OTHER PUBLICATIONS

Al-Ahmad et al., dated 2005, Early experience with a computerized robotically controlled catheter system, Journal of Interventional Cardiac Electrophysiology, 12:199-202.
(Continued)

*Primary Examiner* — Sean D Mattson
(74) *Attorney, Agent, or Firm* — Chang & Hale LLP

(57) ABSTRACT

Navigation of an instrument within a luminal network can include image-based airway analysis and mapping. Image-based airway analysis can include detecting one or more airways in an image captured within a luminal network and determining branching information indicative of how the current airway in which the image is captured branches into the detected "child" airways. Image-based airway mapping can include mapping the one or more detected airways to corresponding expected airways of the luminal network in the preoperative model.

20 Claims, 27 Drawing Sheets

Related U.S. Application Data

(60) Provisional application No. 62/678,881, filed on May 31, 2018.

(51) Int. Cl.
*A61B 1/267* (2006.01)
*A61B 34/30* (2016.01)
*A61B 1/273* (2006.01)
*A61B 17/00* (2006.01)
*A61B 46/10* (2016.01)
*A61B 10/02* (2006.01)
*A61B 1/05* (2006.01)
*A61B 1/307* (2006.01)
*A61B 1/313* (2006.01)

(52) U.S. Cl.
CPC ........ *A61B 1/00149* (2013.01); *A61B 1/2676* (2013.01); *A61B 1/2736* (2013.01); *A61B 34/20* (2016.02); *A61B 34/30* (2016.02); *A61B 1/0002* (2013.01); *A61B 1/05* (2013.01); *A61B 1/307* (2013.01); *A61B 1/3132* (2013.01); *A61B 10/0233* (2013.01); *A61B 46/10* (2016.02); *A61B 2017/00809* (2013.01); *A61B 2034/2055* (2016.02); *A61B 2034/2059* (2016.02); *A61B 2034/2061* (2016.02); *A61B 2034/2065* (2016.02); *G06T 2207/10068* (2013.01); *G06T 2207/20076* (2013.01)

(58) Field of Classification Search
CPC ....... A61B 1/2736; A61B 1/0002; A61B 1/05; A61B 1/307; A61B 1/3132; A61B 1/0676; A61B 1/0684; A61B 1/0016; A61B 1/018; A61B 1/00009; A61B 34/20; A61B 34/30; A61B 34/25; A61B 10/0233; A61B 46/10; A61B 2034/2055; A61B 2034/2059; A61B 2034/2061; A61B 2034/2065; A61B 2034/105; A61B 2034/2048; A61B 2034/2051; A61B 2034/301; A61B 2034/742; A61B 2090/3614; A61B 2090/306; A61B 2090/309; A61B 2090/376; A61B 90/361; A61B 90/37; A61B 2017/00809; G06T 2207/10068; G06T 2207/20076; A61G 13/02

See application file for complete search history.

(56) References Cited

U.S. PATENT DOCUMENTS

| | | | |
|---|---|---|---|
| 5,526,812 A | 6/1996 | Dumoulin et al. |
| 5,550,953 A | 8/1996 | Seraji |
| 5,831,614 A | 11/1998 | Tognazzini et al. |
| 5,935,075 A | 8/1999 | Casscells |
| 6,038,467 A | 3/2000 | De Bliek et al. |
| 6,047,080 A | 4/2000 | Chen |
| 6,059,718 A | 5/2000 | Taniguchi et al. |
| 6,063,095 A | 5/2000 | Wang et al. |
| 6,167,292 A | 12/2000 | Badano |
| 6,203,493 B1 | 3/2001 | Ben-Haim |
| 6,246,784 B1 | 6/2001 | Summers |
| 6,246,898 B1 | 6/2001 | Vesely |
| 6,332,089 B1 | 12/2001 | Acker |
| 6,425,865 B1 | 7/2002 | Salcudean et al. |
| 6,466,198 B1 | 10/2002 | Feinstein |
| 6,490,467 B1 | 12/2002 | Bucholz |
| 6,553,251 B1 | 4/2003 | Lahdesmaki |
| 6,665,554 B1 | 12/2003 | Charles |
| 6,690,963 B2 | 2/2004 | Ben-Haim |
| 6,690,964 B2 | 2/2004 | Bieger et al. |
| 6,755,797 B1 | 6/2004 | Stouffer |
| 6,812,842 B2 | 11/2004 | Dimmer |
| 6,899,672 B2 | 5/2005 | Chin |
| 6,926,709 B2 | 8/2005 | Bieger et al. |
| 7,180,976 B2 | 2/2007 | Wink |
| 7,206,627 B2 | 4/2007 | Abovitz |
| 7,233,820 B2 | 6/2007 | Gilboa |
| 7,386,339 B2 | 6/2008 | Strommer et al. |
| 7,697,972 B2 | 4/2010 | Verard |
| 7,756,563 B2 | 7/2010 | Higgins |
| 7,850,642 B2 | 12/2010 | Moll et al. |
| 7,901,348 B2 | 3/2011 | Soper |
| 8,155,403 B2 | 4/2012 | Tschirren |
| 8,190,238 B2 | 5/2012 | Moll et al. |
| 8,290,571 B2 | 10/2012 | Younge et al. |
| 8,298,135 B2 | 10/2012 | Ito et al. |
| 8,317,746 B2 | 11/2012 | Sewell et al. |
| 8,394,054 B2 | 3/2013 | Wallace et al. |
| 8,460,236 B2 | 6/2013 | Roelle et al. |
| 8,821,376 B2 | 9/2014 | Tolkowsky |
| 8,858,424 B2 | 10/2014 | Hasegawa |
| 8,929,631 B2 | 1/2015 | Pfister et al. |
| 9,014,851 B2 | 4/2015 | Wong et al. |
| 9,084,623 B2 | 7/2015 | Gomez et al. |
| 9,125,639 B2 | 9/2015 | Mathis |
| 9,138,129 B2 | 9/2015 | Diolaiti |
| 9,183,354 B2 | 11/2015 | Baker et al. |
| 9,186,046 B2 | 11/2015 | Ramamurthy et al. |
| 9,272,416 B2 | 3/2016 | Hourtash et al. |
| 9,289,578 B2 | 3/2016 | Walker et al. |
| 9,459,087 B2 | 10/2016 | Dunbar |
| 9,504,604 B2 | 11/2016 | Alvarez |
| 9,561,083 B2 | 2/2017 | Yu et al. |
| 9,603,668 B2 | 3/2017 | Weingarten et al. |
| 9,622,827 B2 | 4/2017 | Yu et al. |
| 9,629,682 B2 | 4/2017 | Wallace et al. |
| 9,636,184 B2 | 5/2017 | Lee et al. |
| 9,710,921 B2 | 7/2017 | Wong et al. |
| 9,713,509 B2 | 7/2017 | Schuh et al. |
| 9,717,563 B2 | 8/2017 | Tognaccini |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,046,140 B2 | 8/2018 | Kokish et al. |
| 10,080,576 B2 | 9/2018 | Romo et al. |
| 10,098,565 B2 | 10/2018 | Brannan et al. |
| 10,123,755 B2 | 11/2018 | Walker et al. |
| 10,130,345 B2 | 11/2018 | Wong et al. |
| 10,136,950 B2 | 11/2018 | Schoenefeld |
| 10,136,959 B2 | 11/2018 | Mintz et al. |
| 10,143,360 B2 | 12/2018 | Roelle et al. |
| 10,143,526 B2 | 12/2018 | Walker et al. |
| 10,145,747 B1 | 12/2018 | Lin et al. |
| 10,149,720 B2 | 12/2018 | Romo |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,251,713 B2 | 4/2019 | Morales et al. |
| 10,278,778 B2 | 5/2019 | State |
| 10,285,574 B2 | 5/2019 | Landey et al. |
| 10,299,870 B2 | 5/2019 | Connolly et al. |
| 10,314,463 B2 | 6/2019 | Agrawal et al. |

(56) References Cited

U.S. PATENT DOCUMENTS

| | | |
|---|---|---|
| 10,383,765 B2 | 8/2019 | Alvarez et al. |
| 10,398,518 B2 | 9/2019 | Yu et al. |
| 10,405,939 B2 | 9/2019 | Romo et al. |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer |
| 10,453,174 B2 | 10/2019 | Popovic et al. |
| 10,492,741 B2 | 10/2019 | Walker et al. |
| 10,464,209 B2 | 11/2019 | Ho et al. |
| 10,470,830 B2 | 11/2019 | Hill |
| 10,482,599 B2 | 11/2019 | Mintz et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan |
| 10,531,864 B2 | 1/2020 | Wong et al. |
| 10,539,478 B2 | 1/2020 | Lin |
| 10,543,048 B2 | 1/2020 | Noonan et al. |
| 10,555,775 B2 | 2/2020 | Hoffman et al. |
| 10,555,778 B2 | 2/2020 | Ummalaneni et al. |
| 10,631,949 B2 | 4/2020 | Schuh et al. |
| 10,639,108 B2 | 5/2020 | Romo et al. |
| 10,639,109 B2 | 5/2020 | Bovay et al. |
| 10,639,114 B2 | 5/2020 | Schuh |
| 10,667,679 B2 | 6/2020 | Higgins et al. |
| 10,667,871 B2 | 6/2020 | Romo et al. |
| 10,667,875 B2 | 6/2020 | DeFonzo |
| 10,682,189 B2 | 6/2020 | Schuh et al. |
| 10,702,348 B2 | 7/2020 | Moll et al. |
| 10,716,461 B2 | 7/2020 | Jenkins |
| 10,743,751 B2 | 8/2020 | Landey et al. |
| 10,744,035 B2 | 8/2020 | Alvarez et al. |
| 10,751,140 B2 | 8/2020 | Wallace et al. |
| 10,765,303 B2 | 9/2020 | Graetzel et al. |
| 10,765,487 B2 | 9/2020 | Ho |
| 10,779,898 B2 | 9/2020 | Hill |
| 10,786,329 B2 | 9/2020 | Schuh et al. |
| 10,786,432 B2 | 10/2020 | Mintz et al. |
| 10,792,464 B2 | 10/2020 | Romo et al. |
| 10,792,466 B2 | 10/2020 | Landey et al. |
| 10,813,539 B2 | 10/2020 | Graetzel et al. |
| 10,814,101 B2 | 10/2020 | Jiang |
| 10,820,947 B2 | 11/2020 | Julian |
| 10,827,913 B2 | 11/2020 | Ummalaneni et al. |
| 10,828,118 B2 | 11/2020 | Schuh |
| 10,835,153 B2 | 11/2020 | Rafii-Tari et al. |
| 10,850,013 B2 | 12/2020 | Hsu |
| 10,881,280 B2 | 1/2021 | Baez |
| 10,881,456 B2 | 1/2021 | Werneth et al. |
| 10,888,248 B2 | 1/2021 | Zhao et al. |
| 10,898,275 B2* | 1/2021 | Ye .................. A61B 1/0676 |
| 10,918,307 B2 | 2/2021 | Olson et al. |
| 11,172,895 B2 | 11/2021 | Dickhans et al. |
| 2001/0021843 A1 | 9/2001 | Bosselmann et al. |
| 2001/0039421 A1 | 11/2001 | Heilbrun |
| 2002/0065455 A1 | 5/2002 | Ben-Haim et al. |
| 2002/0077533 A1 | 6/2002 | Bieger et al. |
| 2002/0120188 A1 | 8/2002 | Brock et al. |
| 2003/0105603 A1 | 6/2003 | Hardesty |
| 2003/0125622 A1 | 7/2003 | Schweikard |
| 2003/0181809 A1 | 9/2003 | Hall et al. |
| 2003/0195664 A1 | 10/2003 | Nowlin et al. |
| 2004/0047044 A1 | 3/2004 | Dalton |
| 2004/0072066 A1 | 4/2004 | Cho et al. |
| 2004/0097806 A1 | 5/2004 | Hunter et al. |
| 2004/0186349 A1 | 9/2004 | Ewers |
| 2004/0249267 A1 | 12/2004 | Gilboa |
| 2004/0263535 A1 | 12/2004 | Birkenbach et al. |
| 2005/0027397 A1 | 2/2005 | Niemeyer |
| 2005/0060006 A1 | 3/2005 | Pflueger |
| 2005/0085714 A1 | 4/2005 | Foley et al. |
| 2005/0107679 A1 | 5/2005 | Geiger |
| 2005/0143649 A1 | 6/2005 | Minai et al. |
| 2005/0143655 A1 | 6/2005 | Satoh |
| 2005/0182295 A1 | 8/2005 | Soper et al. |
| 2005/0182319 A1 | 8/2005 | Glossop |
| 2005/0193451 A1 | 9/2005 | Quistgaard et al. |
| 2005/0197557 A1 | 9/2005 | Strommer et al. |
| 2005/0256398 A1 | 11/2005 | Hastings |
| 2005/0272975 A1 | 12/2005 | McWeeney et al. |
| 2006/0004286 A1 | 1/2006 | Chang |
| 2006/0025668 A1 | 2/2006 | Peterson |
| 2006/0058643 A1 | 3/2006 | Florent |
| 2006/0084860 A1 | 4/2006 | Geiger |
| 2006/0095066 A1 | 5/2006 | Chang |
| 2006/0098851 A1 | 5/2006 | Shoham |
| 2006/0149134 A1 | 7/2006 | Soper et al. |
| 2006/0173290 A1 | 8/2006 | Lavallee et al. |
| 2006/0184016 A1 | 8/2006 | Glossop |
| 2006/0209019 A1 | 9/2006 | Hu |
| 2006/0258935 A1 | 11/2006 | Pile-Spellman et al. |
| 2006/0258938 A1 | 11/2006 | Hoffman et al. |
| 2007/0032826 A1 | 2/2007 | Schwartz |
| 2007/0055128 A1* | 3/2007 | Glossop .................. A61B 1/018 600/407 |
| 2007/0055144 A1 | 3/2007 | Neustadter |
| 2007/0073136 A1 | 3/2007 | Metzger |
| 2007/0083193 A1 | 4/2007 | Werneth |
| 2007/0123748 A1 | 5/2007 | Meglan |
| 2007/0135886 A1 | 6/2007 | Maschke |
| 2007/0156019 A1 | 7/2007 | Larkin et al. |
| 2007/0161857 A1 | 7/2007 | Durant et al. |
| 2007/0167743 A1 | 7/2007 | Honda |
| 2007/0167801 A1 | 7/2007 | Webler et al. |
| 2007/0208252 A1 | 9/2007 | Makower |
| 2007/0253599 A1 | 11/2007 | White et al. |
| 2007/0269001 A1 | 11/2007 | Maschke |
| 2007/0293721 A1 | 12/2007 | Gilboa |
| 2007/0299353 A1 | 12/2007 | Harlev et al. |
| 2008/0071140 A1 | 3/2008 | Gattani |
| 2008/0079421 A1 | 4/2008 | Jensen |
| 2008/0103389 A1 | 5/2008 | Begelman et al. |
| 2008/0118118 A1 | 5/2008 | Berger |
| 2008/0118135 A1 | 5/2008 | Averbach |
| 2008/0123921 A1 | 5/2008 | Gielen et al. |
| 2008/0147089 A1 | 6/2008 | Loh |
| 2008/0161681 A1 | 7/2008 | Hauck |
| 2008/0183064 A1 | 7/2008 | Chandonnet |
| 2008/0183068 A1 | 7/2008 | Carls et al. |
| 2008/0183073 A1 | 7/2008 | Higgins et al. |
| 2008/0183188 A1 | 7/2008 | Carls et al. |
| 2008/0201016 A1 | 8/2008 | Finlay |
| 2008/0207997 A1 | 8/2008 | Higgins et al. |
| 2008/0212082 A1 | 9/2008 | Froggatt et al. |
| 2008/0218770 A1 | 9/2008 | Moll et al. |
| 2008/0221425 A1 | 9/2008 | Olson et al. |
| 2008/0243142 A1 | 10/2008 | Gildenberg |
| 2008/0262297 A1* | 10/2008 | Gilboa .................. A61B 90/57 600/109 |
| 2008/0275349 A1 | 11/2008 | Halperin |
| 2008/0287963 A1 | 11/2008 | Rogers et al. |
| 2008/0300478 A1 | 12/2008 | Zuhars et al. |
| 2008/0306490 A1 | 12/2008 | Lakin et al. |
| 2008/0312501 A1 | 12/2008 | Hasegawa et al. |
| 2009/0030307 A1 | 1/2009 | Govari |
| 2009/0054729 A1 | 2/2009 | Mori |
| 2009/0076476 A1 | 3/2009 | Barbagli et al. |
| 2009/0149867 A1 | 6/2009 | Glozman |
| 2009/0209817 A1 | 8/2009 | Averbuch |
| 2009/0227861 A1 | 9/2009 | Ganatra |
| 2009/0228020 A1 | 9/2009 | Wallace et al. |
| 2009/0248036 A1 | 10/2009 | Hoffman et al. |
| 2009/0259230 A1 | 10/2009 | Khadem |
| 2009/0262109 A1 | 10/2009 | Markowitz et al. |
| 2009/0292166 A1 | 11/2009 | Ito |
| 2009/0295797 A1 | 12/2009 | Sakaguchi |
| 2010/0008555 A1 | 1/2010 | Trumer |
| 2010/0030061 A1 | 2/2010 | Canfield |
| 2010/0039506 A1 | 2/2010 | Sarvestani et al. |
| 2010/0041949 A1 | 2/2010 | Tolkowsky |
| 2010/0054536 A1 | 3/2010 | Huang |
| 2010/0113852 A1 | 5/2010 | Prisco |
| 2010/0121139 A1 | 5/2010 | OuYang |

(56) References Cited

U.S. PATENT DOCUMENTS

| | | |
|---|---|---|
| 2010/0160733 A1 | 6/2010 | Gilboa |
| 2010/0161022 A1 | 6/2010 | Tolkowsky |
| 2010/0161129 A1 | 6/2010 | Costa et al. |
| 2010/0225209 A1 | 9/2010 | Goldberg |
| 2010/0240989 A1 | 9/2010 | Stoianovici |
| 2010/0290530 A1 | 11/2010 | Huang et al. |
| 2010/0292565 A1 | 11/2010 | Meyer |
| 2010/0298641 A1 | 11/2010 | Tanaka |
| 2010/0328455 A1 | 12/2010 | Nam et al. |
| 2011/0054303 A1 | 3/2011 | Barrick |
| 2011/0092808 A1 | 4/2011 | Shachar |
| 2011/0184238 A1* | 7/2011 | Higgins ............... A61B 1/2676 600/117 |
| 2011/0201885 A1 | 8/2011 | Okamura et al. |
| 2011/0234780 A1 | 9/2011 | Ito |
| 2011/0238082 A1 | 9/2011 | Wenderow |
| 2011/0245665 A1 | 10/2011 | Nentwick |
| 2011/0248987 A1 | 10/2011 | Mitchell |
| 2011/0249016 A1 | 10/2011 | Zhang |
| 2011/0257480 A1 | 10/2011 | Takahashi |
| 2011/0270084 A1 | 11/2011 | Choi et al. |
| 2011/0276179 A1 | 11/2011 | Banks et al. |
| 2011/0319910 A1 | 12/2011 | Roelle et al. |
| 2012/0046521 A1 | 2/2012 | Hunter et al. |
| 2012/0056986 A1 | 3/2012 | Popovic |
| 2012/0059248 A1 | 3/2012 | Holsing |
| 2012/0062714 A1 | 3/2012 | Liu |
| 2012/0065481 A1 | 3/2012 | Hunter |
| 2012/0069167 A1 | 3/2012 | Liu et al. |
| 2012/0071782 A1 | 3/2012 | Patil et al. |
| 2012/0082351 A1 | 4/2012 | Higgins |
| 2012/0120305 A1 | 5/2012 | Takahashi |
| 2012/0136372 A1 | 5/2012 | Girbau et al. |
| 2012/0165656 A1 | 6/2012 | Montag |
| 2012/0172712 A1 | 7/2012 | Bar-Tal |
| 2012/0191079 A1 | 7/2012 | Moll et al. |
| 2012/0209069 A1 | 8/2012 | Popovic |
| 2012/0215094 A1 | 8/2012 | Rahimian et al. |
| 2012/0219185 A1 | 8/2012 | Hu |
| 2012/0289777 A1* | 11/2012 | Chopra ............... A61B 1/00055 382/128 |
| 2012/0289783 A1 | 11/2012 | Duindam et al. |
| 2012/0302869 A1 | 11/2012 | Koyrakh |
| 2013/0060146 A1 | 3/2013 | Yang et al. |
| 2013/0144116 A1 | 6/2013 | Cooper et al. |
| 2013/0165945 A9 | 6/2013 | Roelle |
| 2013/0204124 A1 | 8/2013 | Duindam |
| 2013/0225942 A1 | 8/2013 | Holsing |
| 2013/0243153 A1 | 9/2013 | Sra |
| 2013/0246334 A1 | 9/2013 | Ahuja |
| 2013/0259315 A1 | 10/2013 | Angot et al. |
| 2013/0303892 A1 | 11/2013 | Zhao |
| 2013/0345718 A1 | 12/2013 | Crawford |
| 2014/0058406 A1 | 2/2014 | Tsekos |
| 2014/0072192 A1 | 3/2014 | Reiner |
| 2014/0107390 A1 | 4/2014 | Brown |
| 2014/0114180 A1 | 4/2014 | Jain |
| 2014/0148808 A1 | 4/2014 | Inkpen et al. |
| 2014/0142591 A1 | 5/2014 | Alvarez et al. |
| 2014/0180063 A1* | 6/2014 | Zhao ............... G06T 7/75 600/424 |
| 2006/0015096 A1 | 7/2014 | Hauck et al. |
| 2014/0235943 A1 | 8/2014 | Paris |
| 2014/0243849 A1 | 8/2014 | Saglam et al. |
| 2014/0257746 A1 | 9/2014 | Dunbar et al. |
| 2014/0264081 A1 | 9/2014 | Walker et al. |
| 2014/0275988 A1 | 9/2014 | Walker et al. |
| 2014/0276033 A1 | 9/2014 | Brannan |
| 2014/0276937 A1 | 9/2014 | Wong et al. |
| 2014/0296655 A1 | 10/2014 | Akhbardeh et al. |
| 2014/0296657 A1 | 10/2014 | Izmirli |
| 2014/0309527 A1 | 10/2014 | Namati et al. |
| 2014/0343416 A1 | 11/2014 | Panescu |
| 2014/0347353 A1 | 11/2014 | Popovic et al. |
| 2014/0350391 A1 | 11/2014 | Prisco et al. |
| 2014/0357984 A1 | 12/2014 | Wallace et al. |
| 2014/0364739 A1 | 12/2014 | Liu |
| 2014/0364870 A1 | 12/2014 | Alvarez et al. |
| 2015/0051482 A1 | 2/2015 | Liu et al. |
| 2015/0051592 A1 | 2/2015 | Kintz |
| 2015/0054929 A1* | 2/2015 | Ito ............... A61B 1/0005 348/65 |
| 2015/0057498 A1* | 2/2015 | Akimoto ............ A61B 1/00147 600/103 |
| 2015/0073266 A1 | 3/2015 | Brannan |
| 2015/0141808 A1 | 5/2015 | Elhawary |
| 2015/0141858 A1 | 5/2015 | Razavi |
| 2015/0142013 A1 | 5/2015 | Tanner et al. |
| 2015/0164594 A1 | 6/2015 | Romo et al. |
| 2015/0164596 A1 | 6/2015 | Romo et al. |
| 2015/0223725 A1 | 8/2015 | Engel |
| 2015/0223897 A1 | 8/2015 | Kostrzewski et al. |
| 2015/0223902 A1 | 8/2015 | Walker et al. |
| 2015/0255782 A1 | 9/2015 | Kim et al. |
| 2015/0265087 A1 | 9/2015 | Park |
| 2015/0265368 A1 | 9/2015 | Chopra |
| 2015/0275986 A1 | 10/2015 | Cooper |
| 2015/0287192 A1 | 10/2015 | Sasaki |
| 2015/0297133 A1 | 10/2015 | Jouanique-Dubuis et al. |
| 2015/0305650 A1 | 10/2015 | Hunter |
| 2015/0313503 A1 | 11/2015 | Seibel et al. |
| 2015/0335480 A1 | 11/2015 | Alvarez et al. |
| 2016/0000302 A1 | 1/2016 | Brown |
| 2016/0000414 A1 | 1/2016 | Brown |
| 2016/0000520 A1 | 1/2016 | Lachmanovich |
| 2016/0001038 A1 | 1/2016 | Romo et al. |
| 2016/0008033 A1 | 1/2016 | Hawkins et al. |
| 2016/0111192 A1 | 4/2016 | Suzara |
| 2016/0128781 A1 | 5/2016 | Blohm et al. |
| 2016/0128992 A1 | 5/2016 | Hudson |
| 2016/0135908 A1 | 5/2016 | Takahashi et al. |
| 2016/0183841 A1 | 6/2016 | Duindam et al. |
| 2016/0199134 A1 | 7/2016 | Brown et al. |
| 2016/0206389 A1 | 7/2016 | Miller |
| 2016/0213432 A1 | 7/2016 | Flexman |
| 2016/0228032 A1 | 8/2016 | Walker et al. |
| 2016/0270865 A1 | 9/2016 | Landey et al. |
| 2016/0287279 A1 | 10/2016 | Bovay et al. |
| 2016/0287346 A1 | 10/2016 | Hyodo et al. |
| 2016/0314710 A1 | 10/2016 | Jarc |
| 2016/0331469 A1 | 11/2016 | Hall et al. |
| 2016/0360947 A1 | 12/2016 | Iida |
| 2016/0372743 A1 | 12/2016 | Cho et al. |
| 2016/0374541 A1 | 12/2016 | Agrawal et al. |
| 2017/0007337 A1 | 1/2017 | Dan |
| 2017/0023423 A1 | 1/2017 | Jackson |
| 2017/0055851 A1 | 3/2017 | Al-Ali |
| 2017/0079725 A1 | 3/2017 | Hoffman |
| 2017/0079726 A1 | 3/2017 | Hoffman |
| 2017/0100199 A1 | 4/2017 | Yu et al. |
| 2017/0119481 A1 | 5/2017 | Romo et al. |
| 2017/0165011 A1 | 6/2017 | Bovay et al. |
| 2017/0172673 A1 | 6/2017 | Yu et al. |
| 2017/0189118 A1 | 7/2017 | Chopra |
| 2017/0202627 A1 | 7/2017 | Sramek et al. |
| 2017/0209073 A1 | 7/2017 | Sramek et al. |
| 2017/0215808 A1 | 8/2017 | Shimol et al. |
| 2017/0215969 A1 | 8/2017 | Zhai et al. |
| 2017/0238807 A9 | 8/2017 | Vertikov et al. |
| 2017/0258366 A1 | 9/2017 | Tupin |
| 2017/0290631 A1 | 10/2017 | Lee et al. |
| 2017/0296032 A1 | 10/2017 | Li |
| 2017/0296202 A1 | 10/2017 | Brown |
| 2017/0303941 A1 | 10/2017 | Eisner |
| 2017/0325896 A1* | 11/2017 | Donhowe ............ G16H 20/40 |
| 2017/0333679 A1 | 11/2017 | Jiang |
| 2017/0340241 A1 | 11/2017 | Yamada |
| 2017/0340396 A1 | 11/2017 | Romo et al. |
| 2017/0348067 A1 | 12/2017 | Krimsky |
| 2017/0360508 A1 | 12/2017 | Germain et al. |
| 2017/0367782 A1 | 12/2017 | Schuh et al. |
| 2018/0025666 A1 | 1/2018 | Ho et al. |
| 2018/0055576 A1 | 3/2018 | Koyrakh |
| 2018/0055582 A1 | 3/2018 | Krimsky |

(56) References Cited

U.S. PATENT DOCUMENTS

| | | |
|---|---|---|
| 2018/0098690 A1 | 4/2018 | Iwaki |
| 2018/0177556 A1 | 6/2018 | Noonan |
| 2018/0214011 A1 | 8/2018 | Graetzel et al. |
| 2018/0217734 A1 | 8/2018 | Koenig et al. |
| 2018/0220883 A1 | 8/2018 | Higgins et al. |
| 2018/0221038 A1 | 8/2018 | Noonan et al. |
| 2018/0221039 A1 | 8/2018 | Shah |
| 2018/0240237 A1 | 8/2018 | Donhowe et al. |
| 2018/0250083 A1 | 9/2018 | Schuh et al. |
| 2018/0263714 A1 | 9/2018 | Kostrzewski |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0286108 A1 * | 10/2018 | Hirakawa .......... A61B 1/00194 |
| 2018/0289431 A1 | 10/2018 | Draper et al. |
| 2018/0308232 A1 | 10/2018 | Gliner |
| 2018/0308247 A1 | 10/2018 | Gupta |
| 2018/0325499 A1 | 11/2018 | Landey et al. |
| 2018/0333044 A1 | 11/2018 | Jenkins |
| 2018/0360435 A1 | 12/2018 | Romo |
| 2018/0368920 A1 | 12/2018 | Ummalaneni |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000576 A1 | 1/2019 | Mintz et al. |
| 2019/0046814 A1 | 2/2019 | Senden et al. |
| 2019/0066314 A1 | 2/2019 | Abhari |
| 2019/0083183 A1 | 3/2019 | Moll et al. |
| 2019/0086349 A1 | 3/2019 | Nelson |
| 2019/0105776 A1 | 4/2019 | Ho et al. |
| 2019/0105785 A1 | 4/2019 | Meyer et al. |
| 2019/0107454 A1 | 4/2019 | Lin et al. |
| 2019/0110839 A1 | 4/2019 | Rafii-Tari et al. |
| 2019/0110843 A1 | 4/2019 | Ummalaneni |
| 2019/0117176 A1 | 4/2019 | Walker et al. |
| 2019/0117203 A1 | 4/2019 | Wong et al. |
| 2019/0151148 A1 | 4/2019 | Alvarez et al. |
| 2019/0125164 A1 | 5/2019 | Roelle et al. |
| 2019/0142519 A1 | 5/2019 | Siemionow et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175799 A1 | 6/2019 | Hsu et al. |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216550 A1 | 7/2019 | Eyre et al. |
| 2019/0216576 A1 | 7/2019 | Eyre |
| 2019/0223974 A1 | 7/2019 | Romo |
| 2019/0228525 A1 | 7/2019 | Mintz et al. |
| 2019/0228528 A1 | 7/2019 | Mintz et al. |
| 2019/0246882 A1 | 8/2019 | Graetzel et al. |
| 2019/0262086 A1 | 8/2019 | Connolly et al. |
| 2019/0269307 A1 | 9/2019 | Gilboa |
| 2019/0269468 A1 | 9/2019 | Hsu et al. |
| 2019/0274764 A1 | 9/2019 | Romo |
| 2019/0287673 A1 | 9/2019 | Michihata |
| 2019/0290109 A1 | 9/2019 | Agrawal et al. |
| 2019/0298160 A1 | 10/2019 | Ummalaneni et al. |
| 2019/0298458 A1 | 10/2019 | Srinivasan et al. |
| 2019/0298460 A1 | 10/2019 | Al-Jadda |
| 2019/0298465 A1 | 10/2019 | Chin |
| 2019/0328213 A1 | 10/2019 | Landey et al. |
| 2019/0336238 A1 | 11/2019 | Yu |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo et al. |
| 2020/0000533 A1 | 1/2020 | Schuh |
| 2020/0022767 A1 | 1/2020 | Hill et al. |
| 2020/0038123 A1 | 2/2020 | Graetzel |
| 2020/0039086 A1 | 2/2020 | Meyer |
| 2020/0046434 A1 | 2/2020 | Graetzel |
| 2020/0054405 A1 | 2/2020 | Schuh et al. |
| 2020/0054408 A1 | 2/2020 | Schuh et al. |
| 2020/0060516 A1 | 2/2020 | Baez, Jr. |
| 2020/0078103 A1 | 3/2020 | Duindam |
| 2020/0085516 A1 | 3/2020 | DeFonzo |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho et al. |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0155084 A1 | 5/2020 | Walker |
| 2020/0170630 A1 | 6/2020 | Wong |
| 2020/0170720 A1 | 6/2020 | Ummalaneni |
| 2020/0171660 A1 | 6/2020 | Ho |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |
| 2020/0222134 A1 | 7/2020 | Schuh |
| 2020/0237458 A1 | 7/2020 | DeFonzo |
| 2020/0261172 A1 | 8/2020 | Romo |
| 2020/0268459 A1 | 8/2020 | Noonan et al. |
| 2020/0268460 A1 | 8/2020 | Tse |
| 2020/0281787 A1 | 9/2020 | Ruiz |
| 2020/0297437 A1 | 9/2020 | Schuh |
| 2020/0297444 A1 | 9/2020 | Camarillo |
| 2020/0305922 A1 | 10/2020 | Yan et al. |
| 2020/0305983 A1 | 10/2020 | Yampolsky |
| 2020/0305989 A1 | 10/2020 | Schuh |
| 2020/0315717 A1 | 10/2020 | Bovay |
| 2020/0315723 A1 | 10/2020 | Hassan |
| 2020/0323596 A1 | 10/2020 | Moll |
| 2020/0330167 A1 | 10/2020 | Romo |
| 2020/0345216 A1 | 11/2020 | Jenkins |
| 2020/0352420 A1 | 11/2020 | Graetzel |

FOREIGN PATENT DOCUMENTS

| | | |
|---|---|---|
| CN | 101222882 | 7/2008 |
| CN | 101222882 A | 7/2008 |
| CN | 102316817 | 1/2012 |
| CN | 102316817 A | 1/2012 |
| CN | 102458295 | 5/2012 |
| CN | 102458295 A | 5/2012 |
| CN | 102883651 A | 1/2013 |
| CN | 102946801 | 2/2013 |
| CN | 102973317 | 3/2013 |
| CN | 103705307 | 4/2014 |
| CN | 103735313 | 4/2014 |
| CN | 103813748 | 5/2014 |
| CN | 103957832 A | 7/2014 |
| CN | 104010560 A | 8/2014 |
| CN | 104736085 A | 6/2015 |
| CN | 104758066 | 7/2015 |
| CN | 104780826 A | 7/2015 |
| CN | 104797186 A | 7/2015 |
| CN | 105559850 | 5/2016 |
| CN | 105559886 | 5/2016 |
| CN | 105611881 | 5/2016 |
| CN | 106455908 | 2/2017 |
| CN | 106821498 | 6/2017 |
| CN | 104931059 | 9/2018 |
| EP | 3 025 630 | 6/2016 |
| KR | 10-2014-0009359 | 1/2014 |
| KR | 10-1713676 B1 | 3/2017 |
| RU | 2569699 C2 | 11/2015 |
| WO | WO 05/087128 | 9/2005 |
| WO | WO 06/051523 | 5/2006 |
| WO | WO 09/097461 | 6/2007 |
| WO | 2014058838 A1 | 4/2014 |
| WO | WO 15/089013 | 6/2015 |
| WO | WO 16/077419 | 5/2016 |

(56) References Cited

FOREIGN PATENT DOCUMENTS

| WO | WO 16/203727 | 12/2016 |
|---|---|---|
| WO | WO 17/030916 | 2/2017 |
| WO | WO 17/036774 | 3/2017 |
| WO | WO 17/048194 | 3/2017 |
| WO | WO 17/066108 | 4/2017 |
| WO | WO 17/146890 | 8/2017 |
| WO | WO 17/167754 | 10/2017 |

OTHER PUBLICATIONS

Bell et al., 2014, Six DOF motion estimation for teleoperated flexible endoscopes using optical flow: a comparative study, IEEE International Conference on Robotics and Automation.
Ciuti et al., 2012, Intra-operative monocular 30 reconstruction for image-guided navigation in active locomotion capsule endoscopy. Biomedical Robotics and Biomechatronics (Biorob), 4th IEEE Ras & Embs International Conference on IEEE.
Fallavollita et al., 2010, Acquiring multiview C-arm images to assist cardiac ablation procedures, EURASIP Journal on Image and Video Processing, vol. 2010, Article ID 871408, pp. 1-10.
Gutierrez et al., Mar. 2008, A practical global distortion correction method for an image intensifier based x-ray fluoroscopy system, Med. Phys, 35(3):997-1007.
Haigron et al., 2004, Depth-map-based scene analysis for active navigation in virtual angioscopy, IEEE Transactions on Medical Imaging, 23(11):1380-1390.
Hansen Medical, Inc. 2005, System Overview, product brochure, 2 pp., dated as available at http://hansenmedical.com/system.aspx on Jul. 14, 2006 (accessed Jun. 25, 2019 using the internet archive way back machine).
Hansen Medical, Inc. Bibliography, product brochure, 1 p., dated as available at http://hansenmedical.com/bibliography.aspx on Jul. 14, 2006 (accessed Jun. 25, 2019 using the internet archive way back machine).
Hansen Medical, Inc. dated 2007, Introducing the Sensei Robotic Catheter System, product brochure, 10 pp.
Hansen Medical, Inc. dated 2009, Sensei X Robotic Catheter System, product brochure, 5 pp.
Hansen Medical, Inc. Technology Advantages, product brochure, 1 p., dated as available at http://hansenmedical.com/advantages.aspx on Jul. 13, 2006 (accessed Jun. 25, 2019 using the internet archive way back machine).
Kiraly et al, 2002, Three-dimensional Human Airway Segmentation Methods for Clinical Virtual Bronchoscopy, Acad Radiol, 9:1153-1168.
Kiraly et al., Sep. 2004, Three-dimensional path planning for virtual bronchoscopy, IEEE Transactions on Medical Imaging, 23(9):1365-1379.
Konen et al., 1998, The VN-project: endoscopic image processing for neurosurgery, Computer Aided Surgery, 3:1-6.
Kumar et al., 2014, Stereoscopic visualization of laparoscope image using depth information from 3D model, Computer methods and programs in biomedicine 113(3):862-868.
Livatino et al., 2015, Stereoscopic visualization and 3-D technologies in medical endoscopic teleoperation, IEEE.
Luo et al., 2010, Modified hybrid bronchoscope tracking based on sequential monte carlo sampler: Dynamic phantom validation, Asian Conference on Computer Vision. Springer, Berlin, Heidelberg.
Marrouche et al., dated May 6, 2005, AB32-1, Preliminary human experience using a novel robotic catheter remote control, Heart Rhythm, 2(5):S63.
Mayo Clinic, Robotic Surgery, https://www.mayoclinic.org/tests-procedures/robotic-surgery/about/pac-20394974?p=1, downloaded from the internet on Jul. 12, 2018, 2 pp.
Mourgues et al., 2002, Flexible calibration of actuated stereoscopic endoscope for overlay in robot assisted surgery, International Conference on Medical Image Computing and Computer-Assisted Intervention. Springer, Berlin, Heidelberg.
Nadeem et al., 2016, Depth Reconstruction and Computer-Aided Polyp Detection in Optical Colonoscopy Video Frames, arXiv preprint arXiv:1609.01329.
Oh et al., dated May 2005, P5-75, Novel robotic catheter remote control system: safety and accuracy in delivering RF Lesions in all 4 cardiac chambers, Heart Rhythm, 2(5):S277-S278.
Point Cloud, Sep. 10, 2010, Wikipedia, 2 pp.
Racadio et al., Dec. 2007, Live 3D guidance in the interventional radiology suite, AJR, 189:W357-W364.
Reddy et al., May 2005, P1-53. Porcine pulmonary vein ablation using a novel robotic catheter control system and real-time integration of CT imaging with electoanatomical mapping, Hearth Rhythm, 2(5):S121.
Ren et al., 2011, Multisensor data fusion in an integrated tracking system for endoscopic surgery, IEEE Transactions on Information Technology in Biomedicine, 16(1):106-111.
Sato et al., 2016, Techniques of stapler-based navigational thoracoscopic segmentectomy using virtual assisted lung mapping (VAL-MAP), Journal of Thoracic Disease, 8(Suppl 9):S716.
Shen et al., 2015, Robust camera localisation with depth reconstruction for bronchoscopic navigation. International Journal of Computer Assisted Radiology and Surgery, 10(6):801-813.
Shi et al., Sep. 14-18, 2014, Simultaneous catheter and environment modeling for trans-catheter aortic valve implantation, IEEE/RSJ international Conference on Intelligent Robots and Systems, pp. 2024-2029.
Slepian, dated 2010, Robotic Catheter Intervention: the Hansen Medical Sensei Robot Catheter System, PowerPoint presentation, 28 pp.
Solheim et al., May 14, 2009, Navigated resection of giant intracranial meningiomas based on intraoperative 3D ultrasound, Acta Neurochir, 151:1143-1151.
Solomon et al., Dec. 2000, Three-dimensional CT- Guided Bronchoscopy With a Real-Time Electromagnetic Position Sensor A Comparison of Two Image Registration Methods, Chest, 118(6):1783-1787.
Song et al., 2012, Autonomous and stable tracking of endoscope instrument tools with monocular camera, Advanced Intelligent Mechatronics (AIM), 2012 IEEE-ASME International Conference on. IEEE.
Vemuri et al., Dec. 2015, Inter-operative biopsy site relocations in endoluminal surgery, IEEE Transactions on Biomedical Engineering, Institute of Electrical and Electronics Engineers, <10.1109/TBME.2015.2503981>. <hal-01230752>.
Verdaasdonk et al., Jan. 23, 2012, Effect of microsecond pulse length and tip shape on explosive bubble formation of 2.78 μm Er,Cr;YSGG and 2.94 μm Er:YAG laser, Proceedings of SPIE, vol. 8221, 12.
Wilson et al., 2008, a buyer's guide to electromagnetic tracking systems for clinical applications, Proc. of SPCI, 6918:691828-1 p. 6918B-11.
Yip et al., 2012, Tissue tracking and registration for image-guided surgery, IEEE transactions on medical imaging 31(11):2169-2182.
Zhou et al., 2010, Synthesis of stereoscopic views from monocular endoscopic videos, Computer Vision and Pattern Recognition Workshops (CVPRW), 2010 IEEE Computer Society Conference on IEEE.
International search report and written opinion dated Aug. 26, 2019 for PCT/US2019/34694.
CN Office Action for Appl. No. 201980003358, dated May 16, 2022, 7 pages.
EP Search Report for Appl. No. 19811290.6, dated Jun. 7, 2022, 12 pages.
Gutierrez et al., Mar. 2008, A Practical Global Distortion Correction Method for an Image Intensifier Based X-Ray Fluoroscopy System, Med. Phys, 35(3)1997-1007, 11 pages.
International Search Report and Written Opinion, dated Aug. 26, 2019 for App. No. PCT/US2019/34694, 8 pages.
Kiraly et al., 2002, Three-dimensional Human Airway Segmentation Methods for Clinical Virtual Bronchoscopy, Acad Radiol, 9:1153-1168, 16 pages.

(56) References Cited

OTHER PUBLICATIONS

Kiraly et al., Sep. 2004, Three-dimensional path planning for virtual bronchoscopy, IEEE Transactions on Medical Imaging, 23(9):1365-1379, 15 pages.

Kumar et al., 2014, Stereoscopic visualization of laparoscope image using depth information from 3D model, Computer methods and programs in biomedicine 113(3):862-868, 7 pages.

Livatino et al., 2015, Stereoscopic visualization and 3-D technologies in medical endoscopic teleoperation, IEEE, 11 pages.

Marrouche et al., dated May 6, 2005, AB32-1, Preliminary human experience using a novel robotic catheter remote control, Heart Rhythm, 2(5):S63, 1 page.

Mayo Clinic, Robotic Surgery, https://www.mayoclinic.org/tests-procedures/robotic-surgery/about/pac-20394974?p=1, downloaded from the internet on Jul. 12, 2018, 2 pgs.

Mourgues et al., 2002, Flexible calibration of actuated stereoscopic endoscope for overlay in robot 672 assisted surgery, International Conference on Medical Image Computing and Computer-Assisted Intervention. SprinQer, Berlin, HeidelberQ, 10 pages.

Nadeem et al., 2016, Depth Reconstruction and Computer-Aided Polyp Detection in Optical Colonoscopy Video Frames, arXiv preprint arXiv:1609.01329, 12 pages.

Non-Final Rejection for U.S. Appl. No. 16/427,092, dated Jan. 9, 2020, 19 pages.

Notice of Allowance for U.S. Appl. No. 16/427,092, dated Aug. 17, 2020, 12 pages.

Notice of Allowance for U.S. Appl. No. 16/427,092, dated Nov. 30, 2020, 7 pages.

Slepian, dated 2010, Robotic Catheter Intervention: the Hansen Medical Sensei Robot Catheter System, PowerPoint presentation, 28 pages.

Verdaasdonk et al., Jan. 23, 2012, Effect of Microsecond Pulse Length and Tip Shape on Explosive Bubble Formation of 2.78 μm Er,Cr;YSGG and 2.94 μm Er:YAG laser, Proceedings of SPIE, vol. 8221, 12, 1 pages.

Wilson et al., 2008, A Buyer's Guide to Electromagnetic Tracking Systems for Clinical Applications, Proc. of SPCI, 6918:691828-1, 12 pages.

\* cited by examiner

IMAGE-BASED AIRWAY ANALYSIS AND MAPPING

CROSS-REFERENCE TO RELATED APPLICATION

This application is a continuation of U.S. application Ser. No. 16/427,092, filed May 30, 2019 and titled "IMAGE-BASED AIRWAY ANALYSIS AND MAPPING," which claims the benefit of U.S. Provisional Application No. 62/678,881, filed May 31, 2018, which is hereby incorporated by reference in its entirety.

TECHNICAL FIELD

This disclosure relates generally to systems and methods for navigation of medical instruments, and more particularly to image-based airway analysis and mapping for navigating robotically-controlled medical instruments.

BACKGROUND

Medical procedures such as endoscopy (e.g., bronchoscopy) may involve accessing and visualizing the inside of a patient's lumen (e.g., airways) for diagnostic and/or therapeutic purposes. During a procedure, a flexible tubular tool or instrument, such as an endoscope, may be inserted into the patient's body. In some instances, a second instrument can be passed through the endoscope to a tissue site identified for diagnosis and/or treatment.

Bronchoscopy is a medical procedure that allows a physician to examine the inside conditions of airways in a patient's lungs, such as bronchi and bronchioles. During the medical procedure, a thin, flexible tubular tool or instrument, known as a bronchoscope, may be inserted into the patient's mouth and passed down the patient's throat into his or her lung airways towards a tissue site identified for subsequent diagnosis and/or treatment. The bronchoscope can have an interior lumen (a "working channel") providing a pathway to the tissue site, and catheters and various medical tools can be inserted through the working channel to the tissue site.

In certain medical procedures, surgical robotic systems may be used to control the insertion and/or manipulation of the surgical tools. Surgical robotic systems may include at least one robotic arm or other instrument positioning device including a manipulator assembly used to control the positioning of the surgical tool during the procedures.

SUMMARY

Robotically-enabled medical systems can be used to perform a variety of medical procedures, including both minimally invasive procedures, such as laparoscopic procedures, and non-invasive procedures, such as endoscopic procedures. Among endoscopic procedures, robotically-enabled medical systems can be used to perform bronchoscopy, ureteroscopy, gastroenterology, etc. During such procedures, a physician and/or computer system can navigate a medical instrument through a luminal network of a patient. The luminal network can include a plurality of branched lumens (such as in bronchial or renal networks), or a single lumen (such as a gastrointestinal tract). The robotically-enabled medical systems can include navigation systems for guiding (or assisting with the guidance of) the medical instrument through the luminal network.

Embodiments of this disclosure relate to systems and techniques for image-based airway analysis and mapping. Image-based airway analysis and mapping may aid navigation through the luminal network. Image-based airway analysis can include identifying, within an image captured with an imaging device on the instrument, one or more airways associated with one or more branches of a luminal network and determining branching information indicative of how the current airway in which the image is captured branches into the detected "child" airways. Image-based airway mapping can include mapping the identified airways to corresponding branches of the luminal network. These systems and techniques may be used to determine or estimate the position of an instrument within the luminal network. The systems, methods, and devices of this disclosure each have several innovative aspects, no single one of which is solely responsible for the desirable attributes disclosed herein.

In one aspect, there is provided a method of navigating an instrument through a luminal network, the method comprising: capturing a plurality of images within the luminal network with an imaging device positioned on the instrument, the plurality of images comprising at least a first image captured at a first time and a second image captured at a second time subsequent to the first time; identifying a first airway in the first image; identifying two or more airways in the second image; determining, based on the first airway in the first image and the two or more airways in the second image, that an overlap condition is met; accessing preoperative model data indicative of an expected count of airways corresponding to a location of the instrument during the second time; and determining, based on the preoperative model data and the determination that the overlap condition is met, a mapping between the two or more airways in the second image and the airways in the preoperative model data.

In another aspect, there is provided a non-transitory computer readable storage medium having stored thereon instructions that, when executed, cause a processor of a device to at least: capture a plurality of images within a luminal network with an imaging device positioned on an instrument, the plurality of images comprising at least a first image captured at a first time and a second image captured at a second time subsequent to the first time; identify a first airway in the first image; identify two or more airways in the second image; determine, based on the first airway in the first image and the two or more airways in the second image, that an overlap condition is met; access preoperative model data indicative of an expected count of airways corresponding to a location of the instrument during the second time; and determine, based on the preoperative model data and the determination that the overlap condition is met, a mapping between the two or more airways in the second image and the airways in the preoperative model data.

In yet another aspect, there is provided a robotic surgical system for mapping one or more airways in a luminal network, the system comprising: an instrument having: an elongate body configured to be inserted into the luminal network, and an imaging device positioned on a distal portion of the elongate body; an instrument positioning device attached to the instrument, the instrument positioning device configured to move the instrument through the luminal network; at least one computer-readable memory having stored thereon executable instructions; and one or more processors in communication with the at least one computer-readable memory and configured to execute the instructions to cause the system to at least: capture a plurality of images within the luminal network with an imaging device positioned on the instrument, the plurality of images comprising at least a first image captured at a first time and a second image captured at a second time subsequent to the first time; identify a first airway in the first image; identify two or more airways in the second image; determine, based on the first airway in the first image and the two or more airways in the second image, that an overlap condition is met; access preoperative model data indicative of an expected count of airways corresponding to a location of the instrument during the second time; and determine, based on the preoperative model data and the determination that the overlap condition is met, a mapping between the two or more airways in the second image and the airways in the preoperative model data.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

I. Overview

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart

Figure 1:
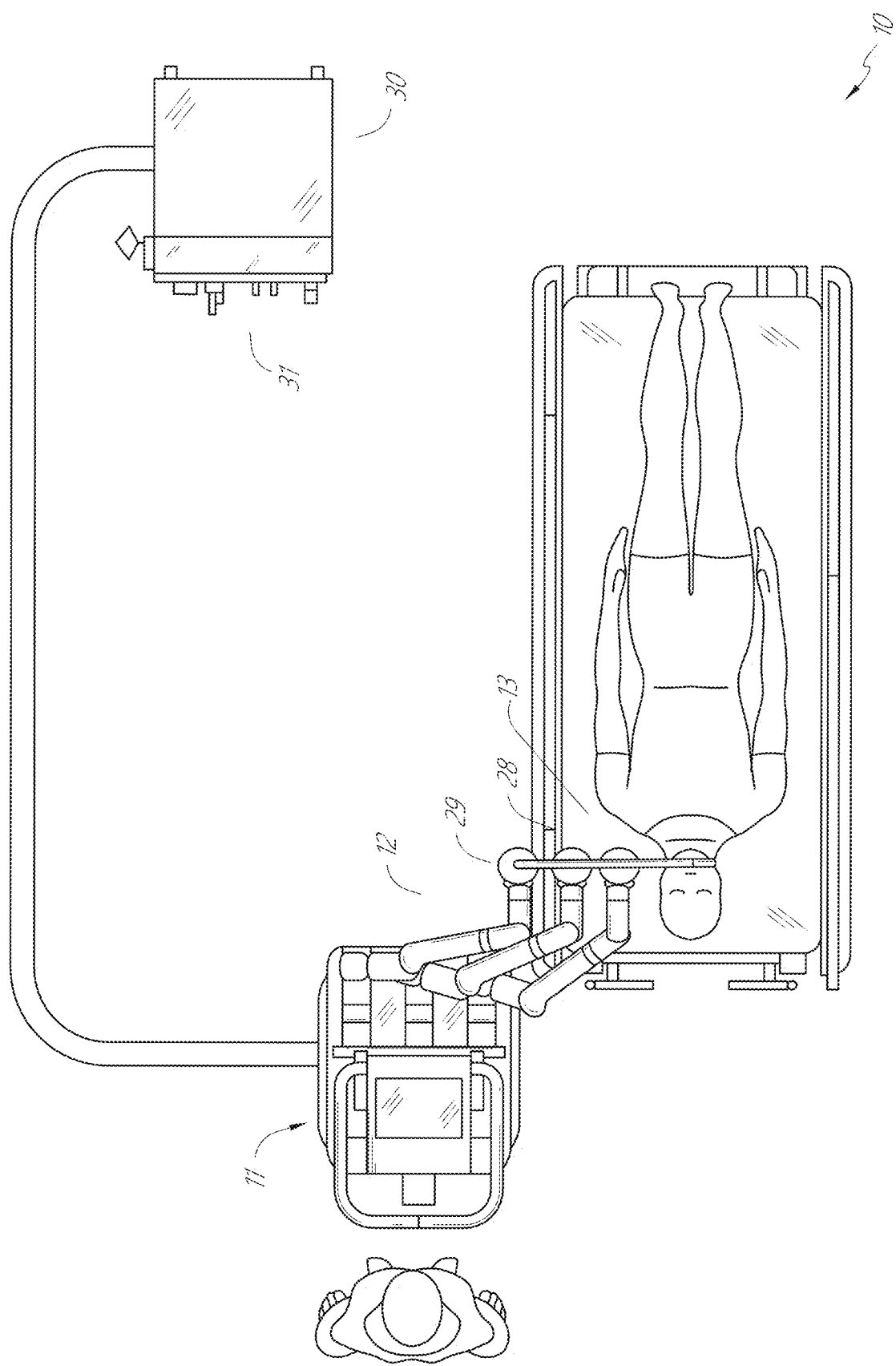
FIG. 1 illustrates an embodiment of a cart-based robotic system arranged for diagnostic and/or therapeutic bronchoscopy procedure(s).
Figure 2:
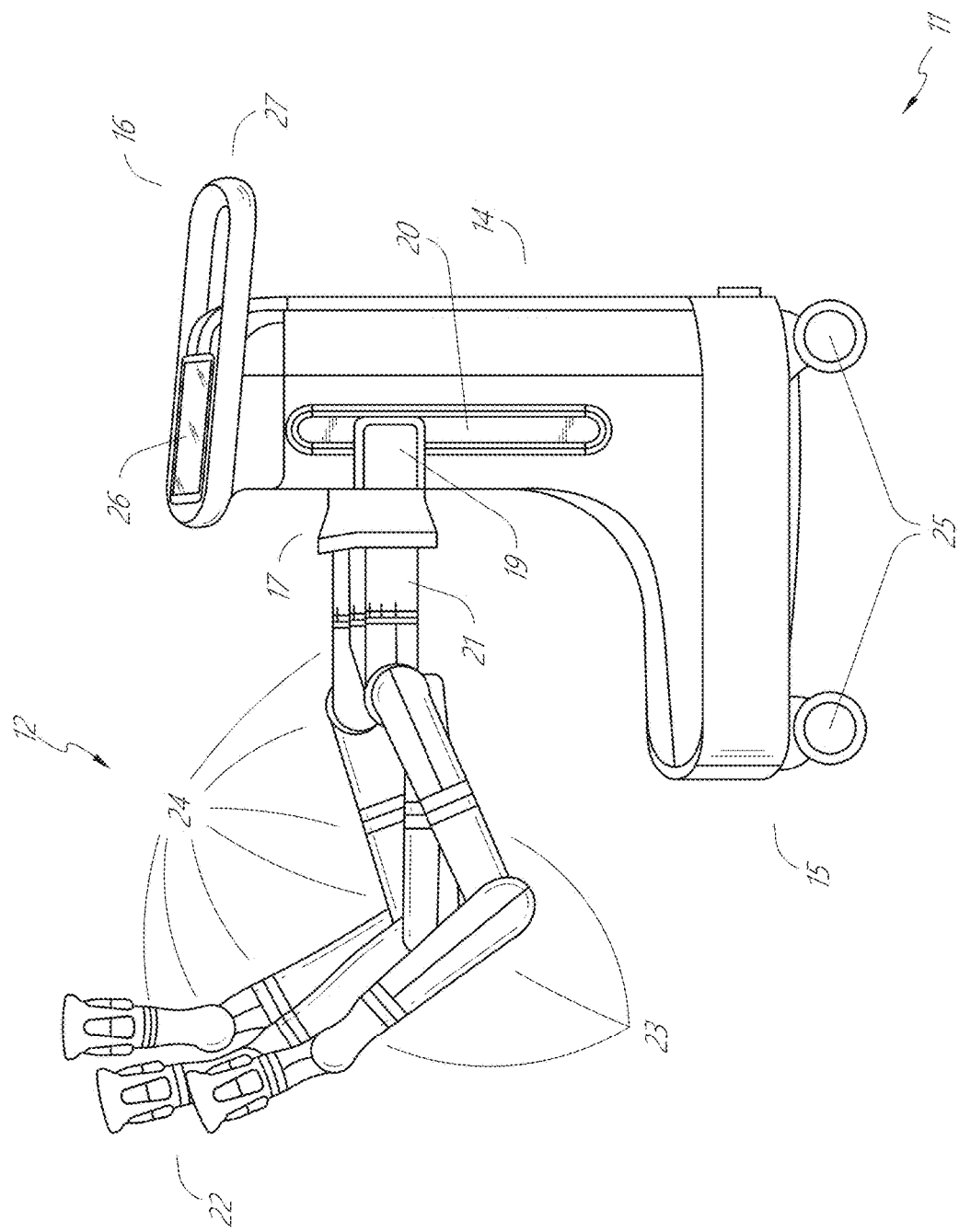
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI)

procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 30 is housed in a body that is separate from the tower 30.

The tower 30 may be coupled to the cart 11 and the endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include preoperative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
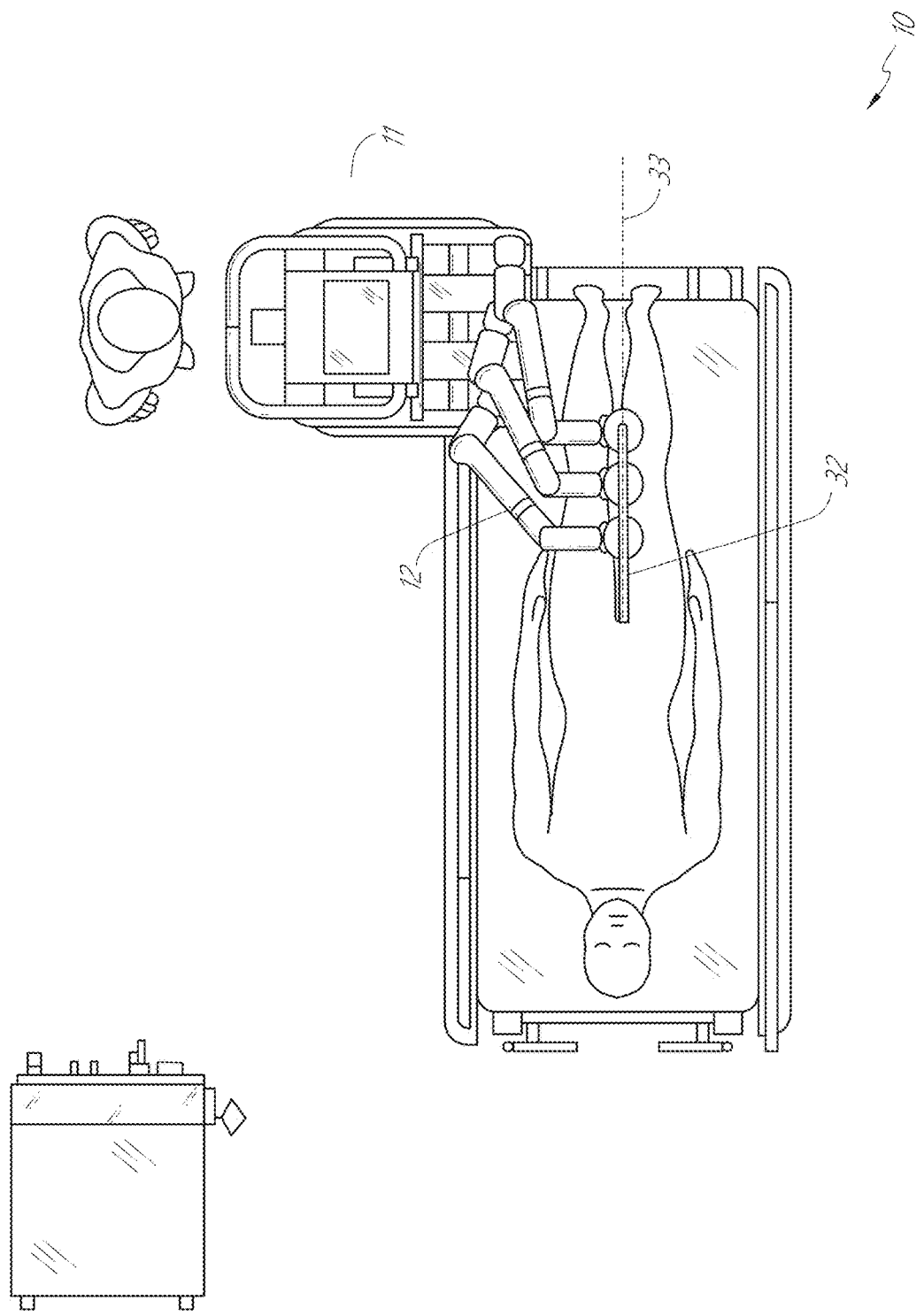
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopy procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
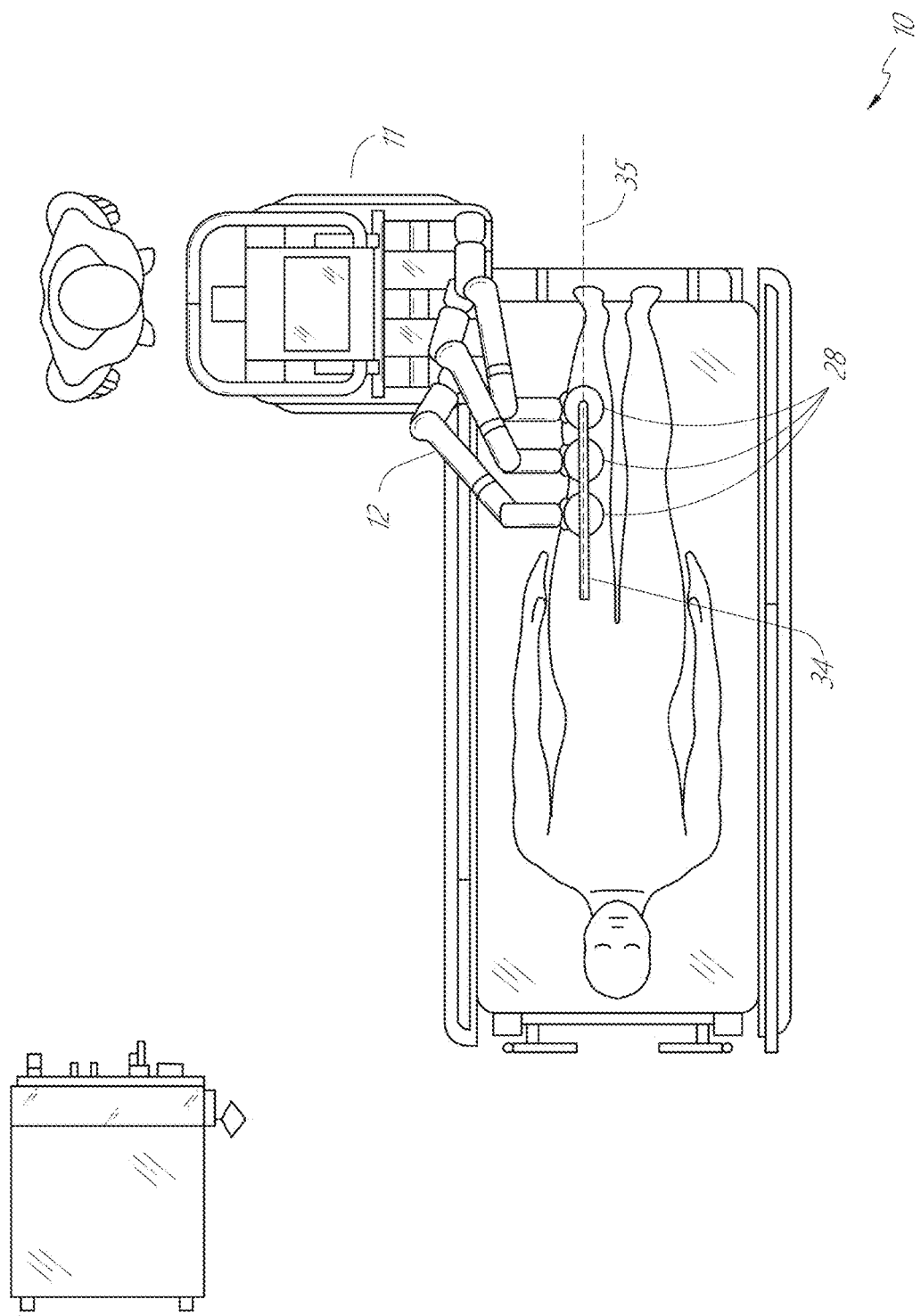
FIG. 4 illustrates an embodiment of the robotic system of FIG. 1 arranged for a vascular procedure.

FIG. 4 illustrates an embodiment of a robotically-enabled system 10 similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopy procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart 11 may be positioned around the patient's upper abdomen in order to reach alternative vascular access points, such as, for example, the carotid and brachial arteries near the shoulder and wrist.

B. Robotic System—Table

Figure 5:
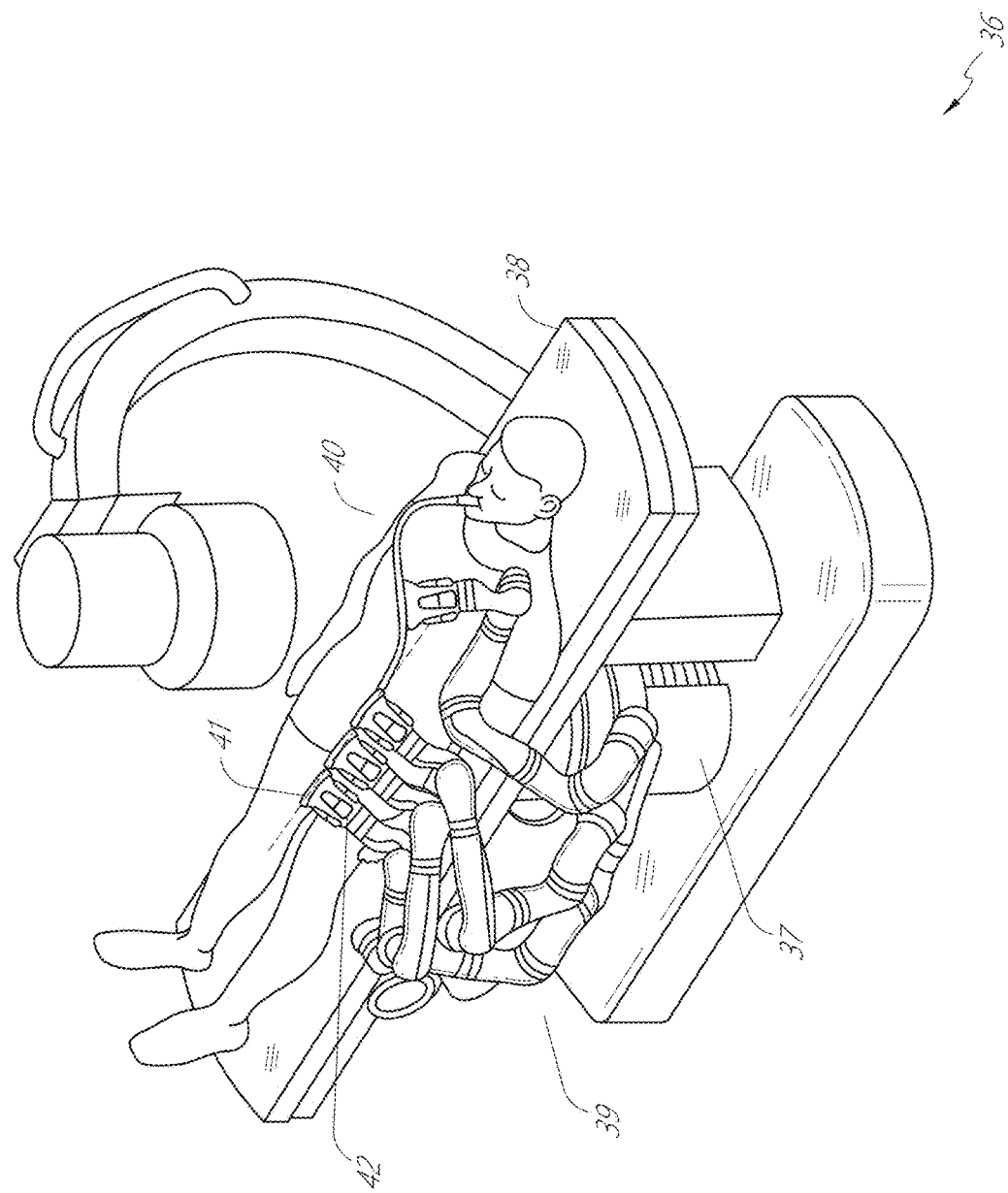
FIG. 5 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
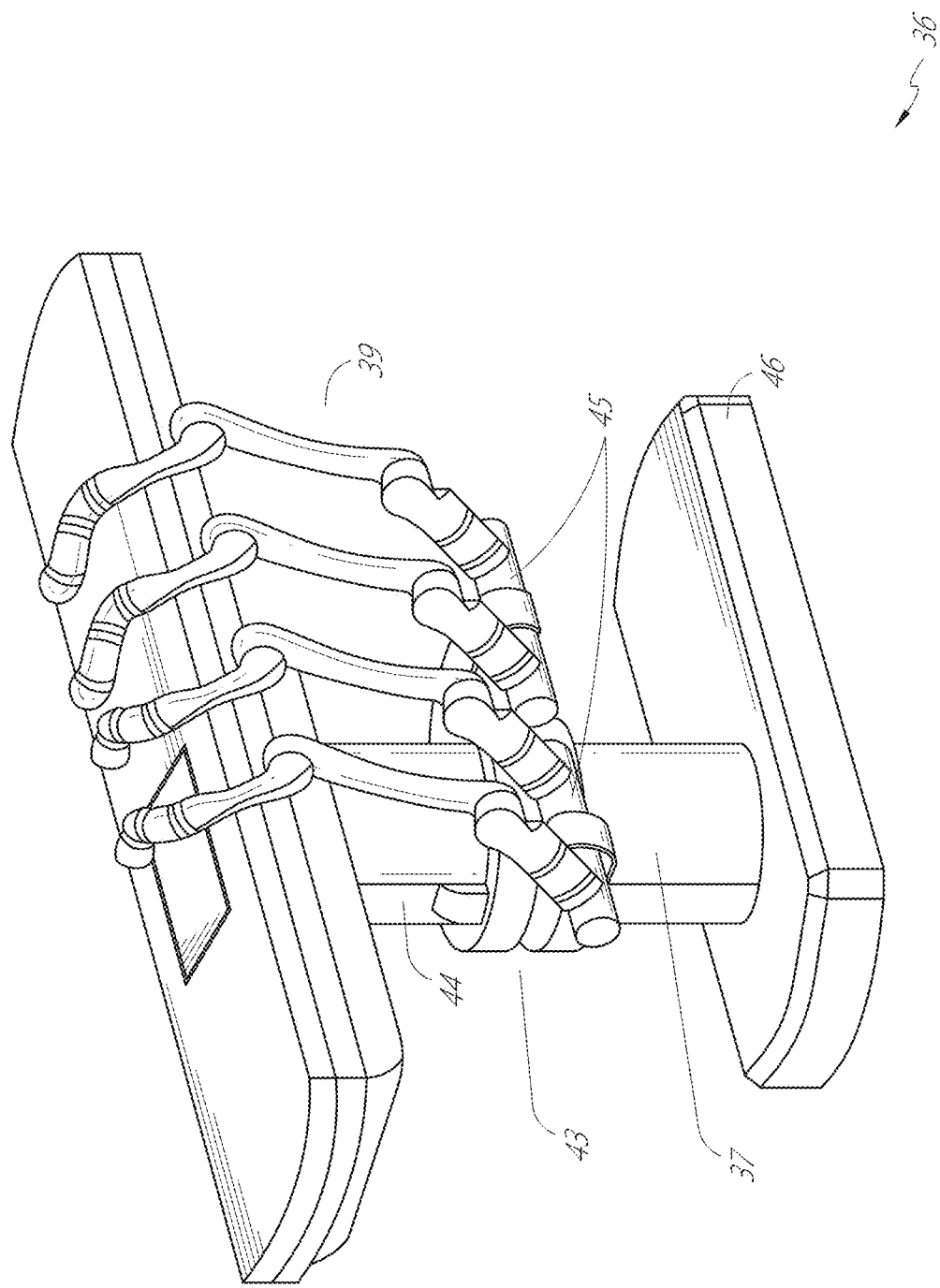
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
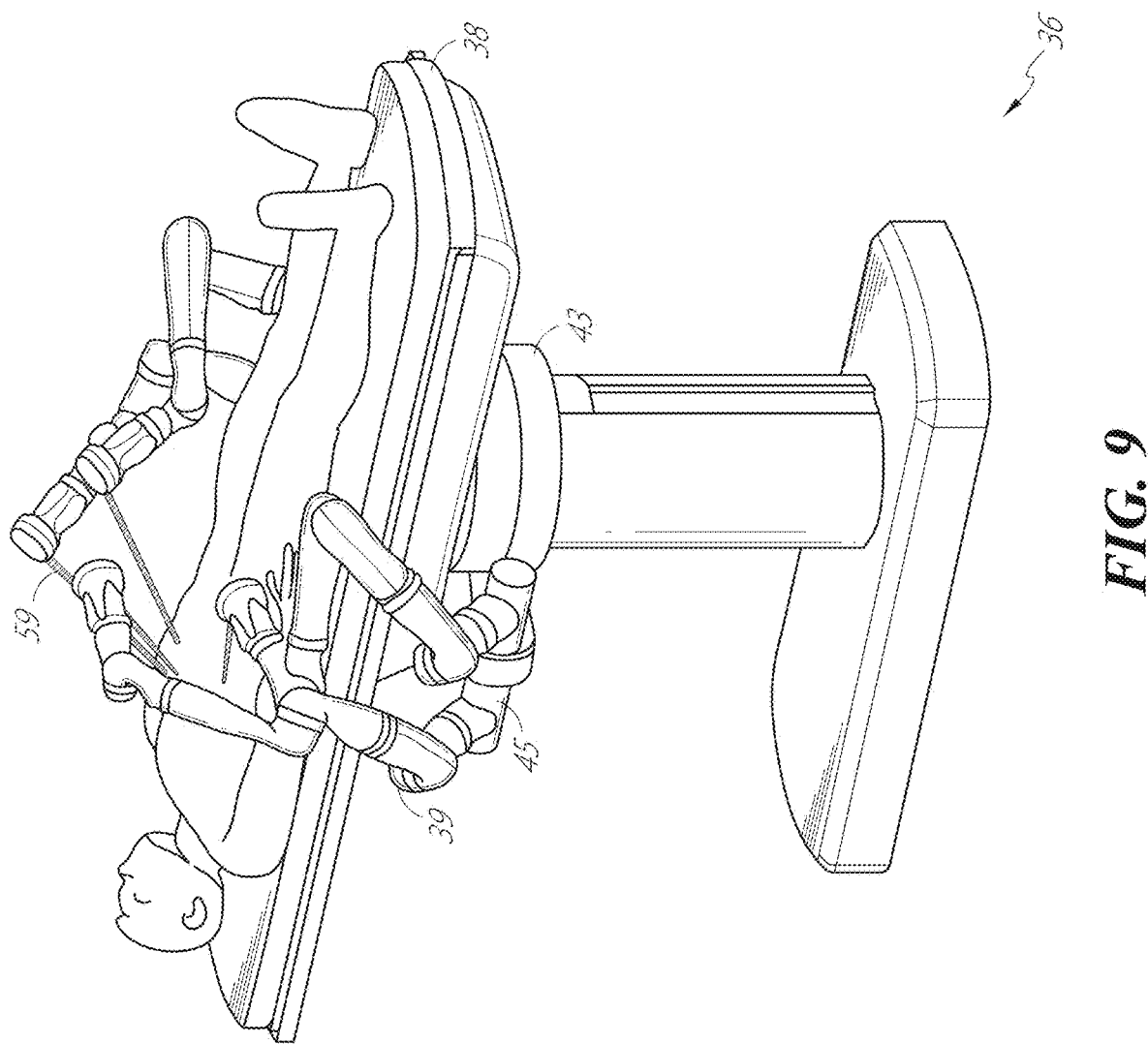
FIG. 9 illustrates an embodiment of a table-based robotic system configured for a laparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages 43, and motors to mechanize the translation of the carriages 43 based the lead screws. The column 37 may also convey power and control signals to the carriages 43 and the robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may be provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intra-operative information, such as real-time imaging, navigation, and tracking information. In some embodiments, the tower may also contain holders for gas tanks to be used for insufflation.

Figure 7:
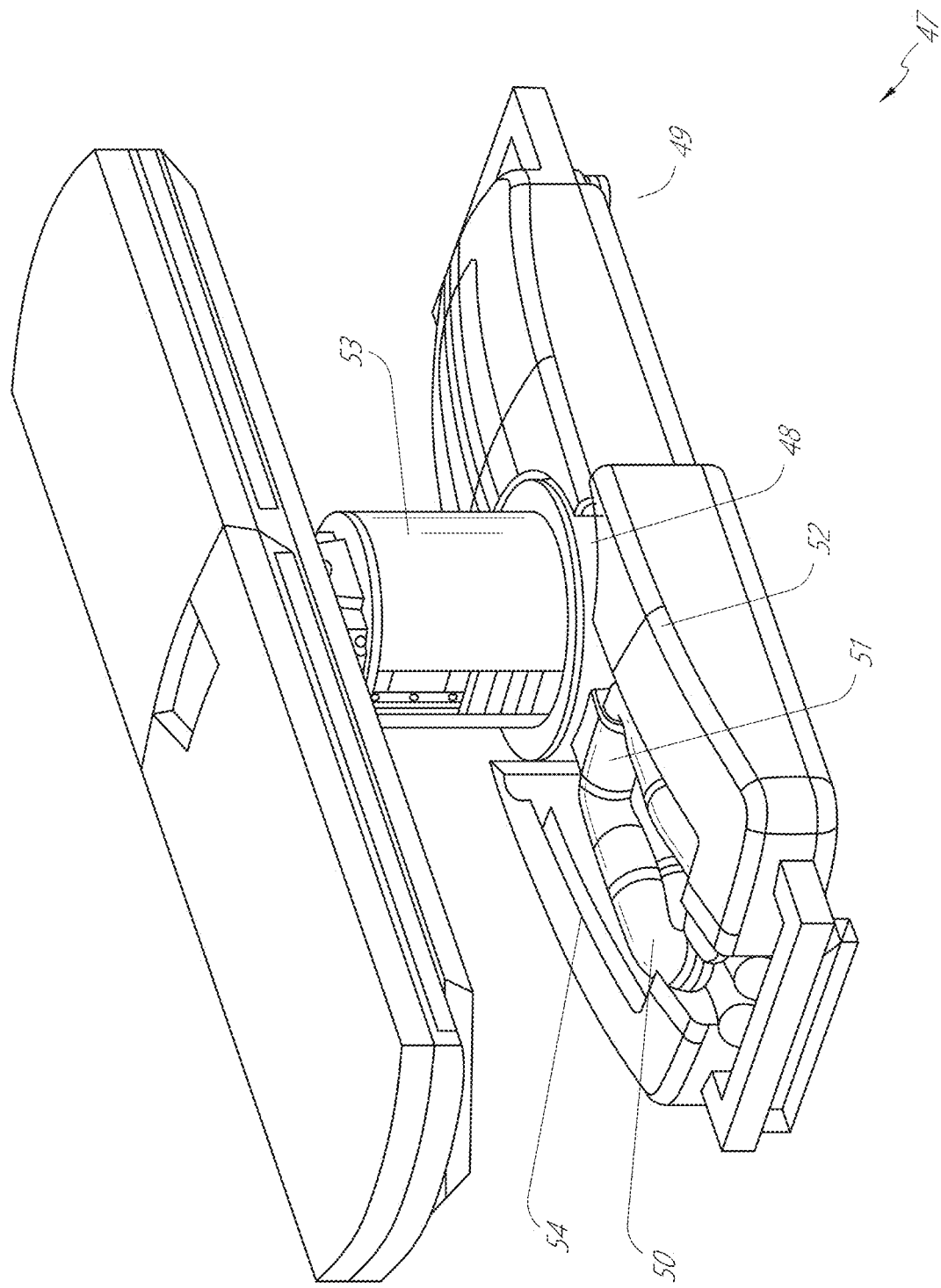
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
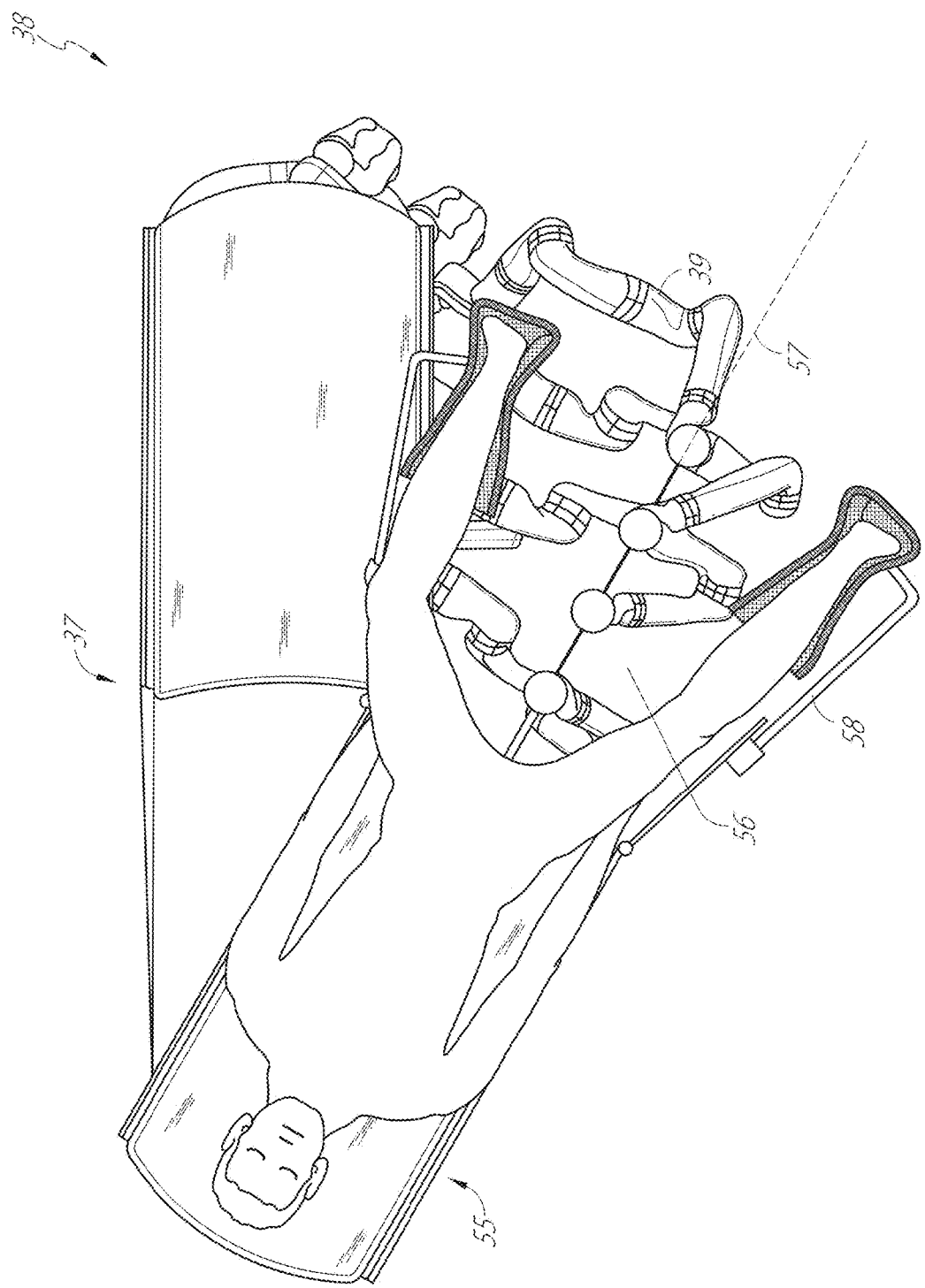
FIG. 8 illustrates an embodiment of a table-based robotic system configured for a ureteroscopy procedure.

FIG. 8 illustrates an embodiment of a robotically-enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopy procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopy procedure. As shown, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
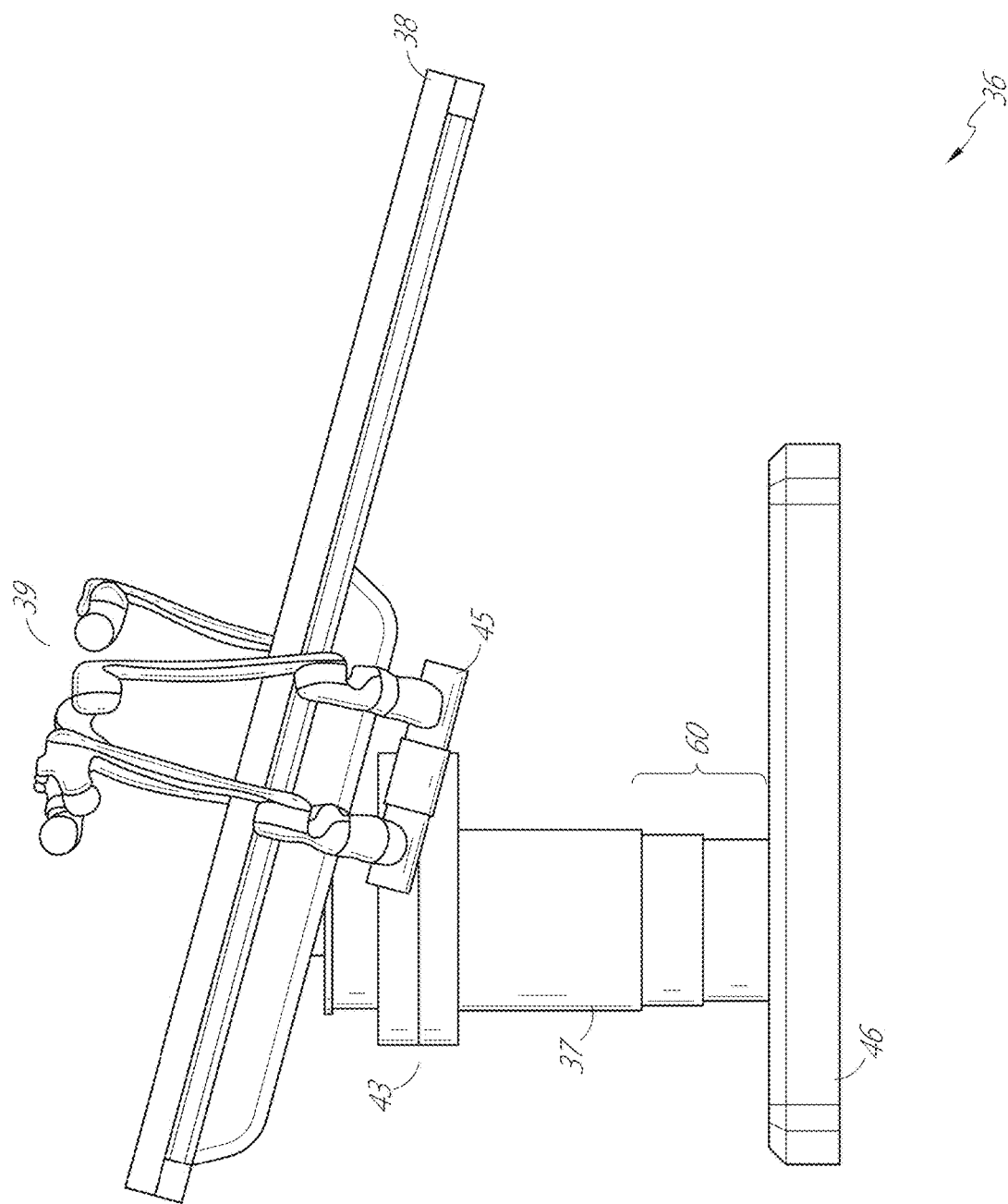
FIG. 10 illustrates an embodiment of the table-based robotic system of FIGS. 5-9 with pitch or tilt adjustment.

To accommodate laparoscopy procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
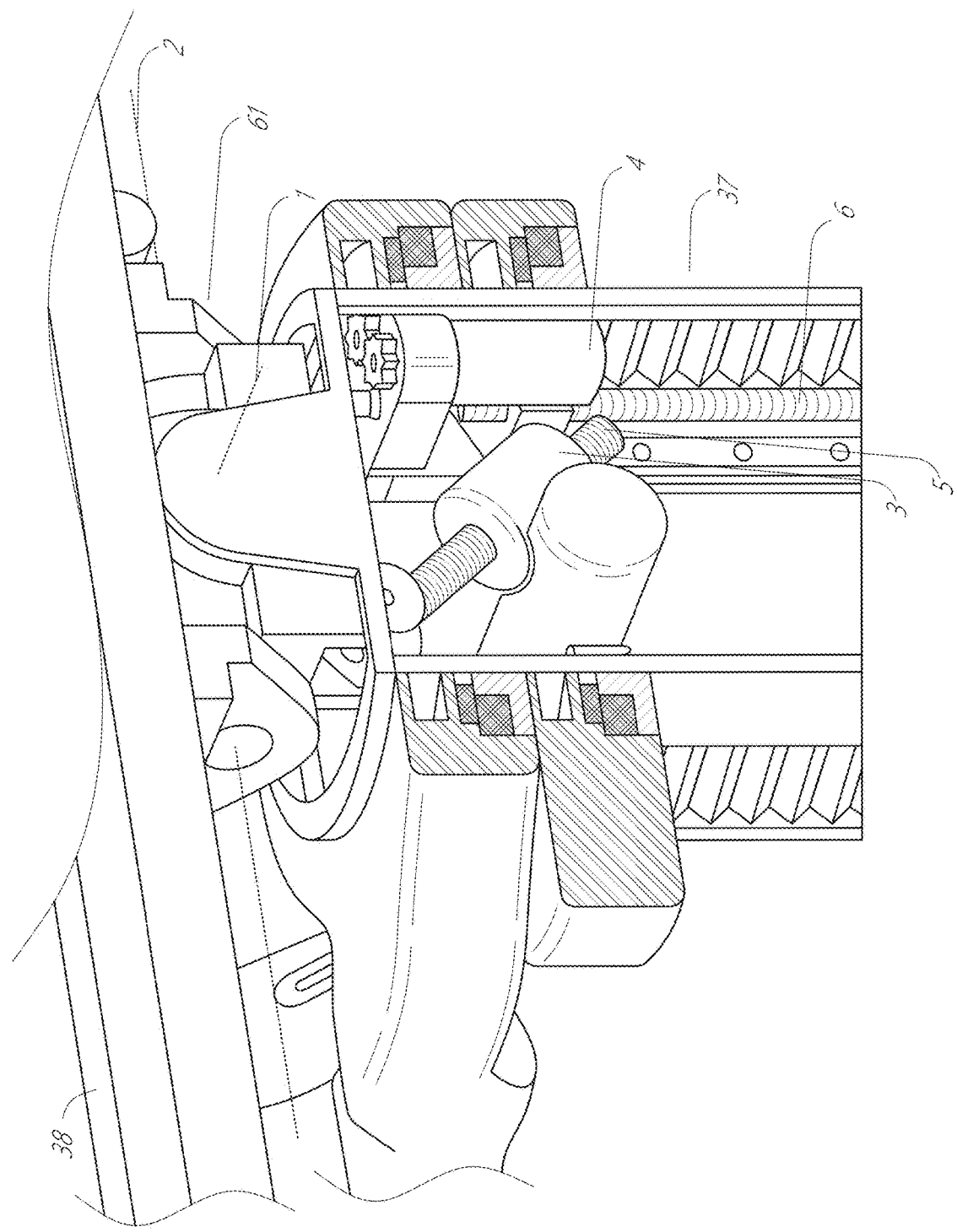
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

C. Instrument Driver & Interface

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 12:
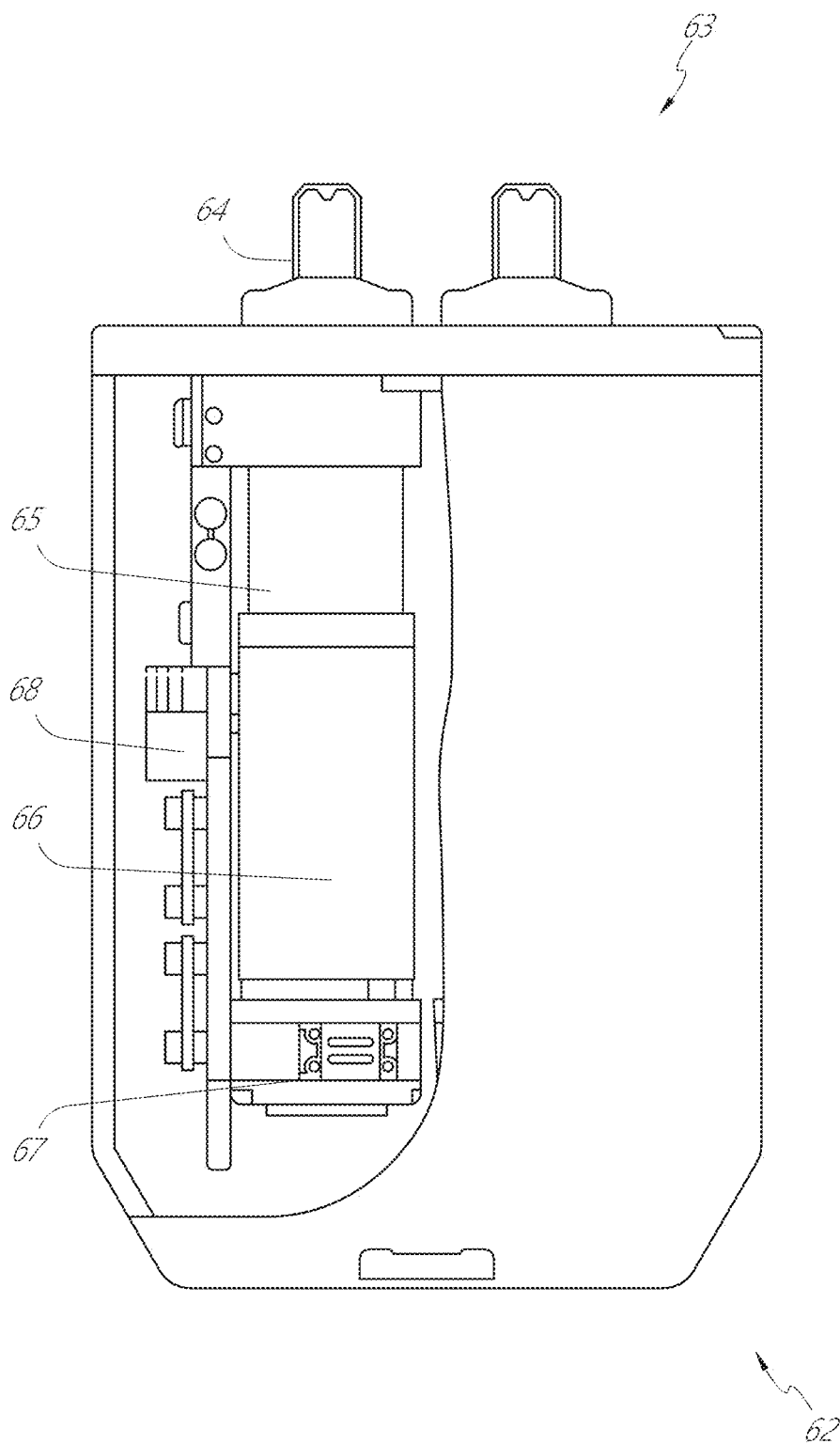
FIG. 12 illustrates an exemplary instrument driver.
Figure 13:
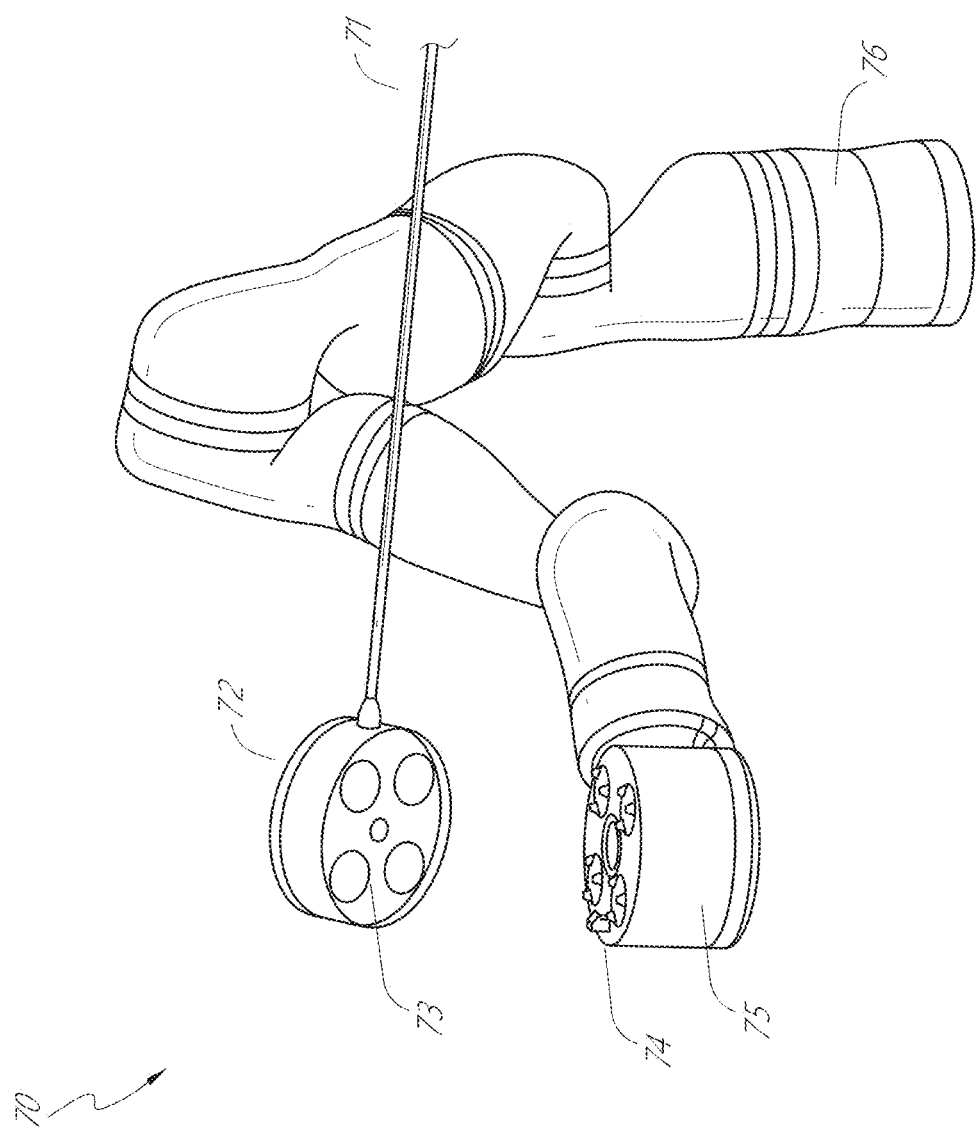
FIG. 13 illustrates an exemplary medical instrument with a paired instrument driver.
Figure 14:
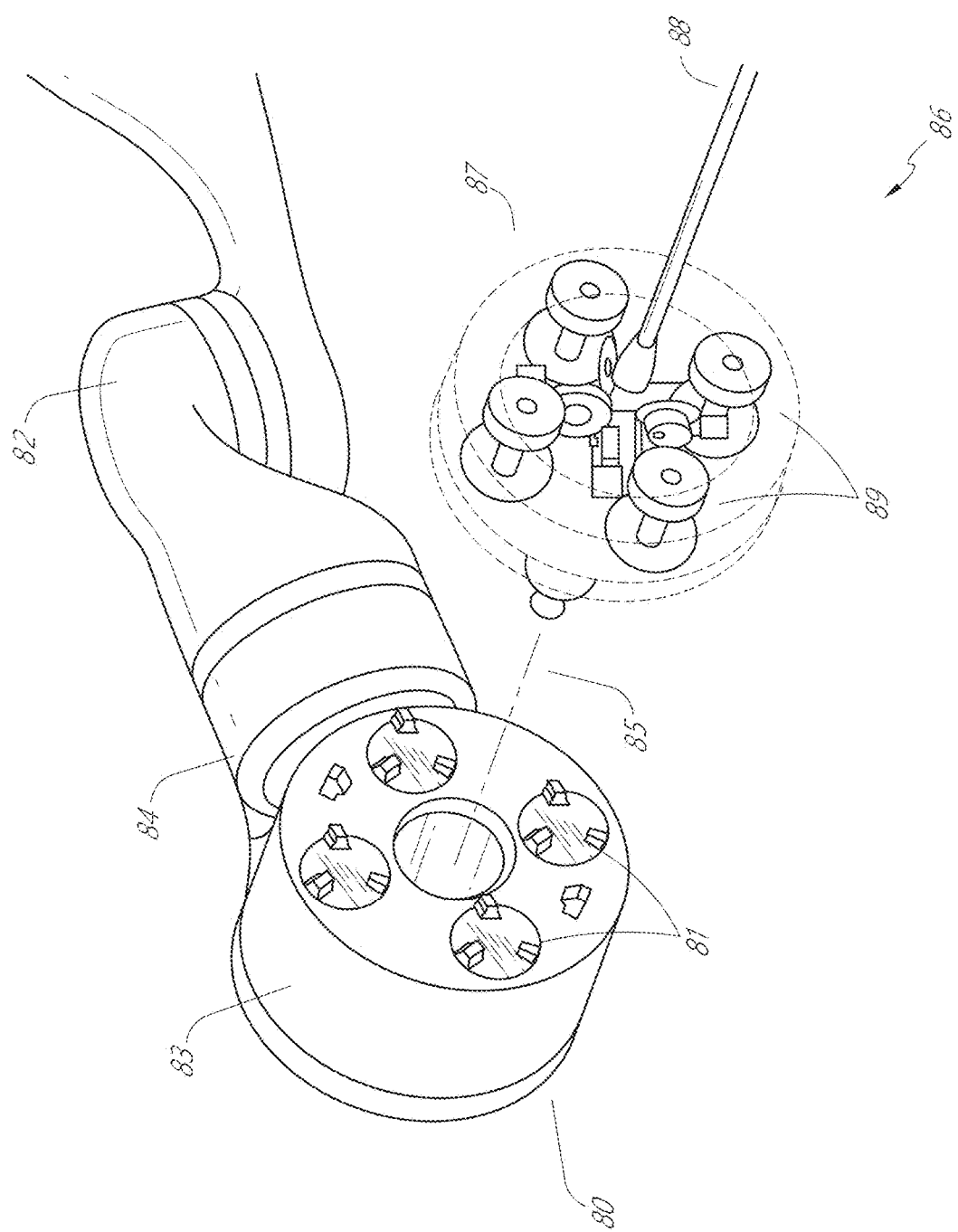
FIG. 14 illustrates an alternative design for an instrument driver and instrument where the axes of the drive units are parallel to the axis of the elongated shaft of the instrument.

FIG. 12 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 may be independently controlled and motorized, and the instrument driver 62 may provide multiple (e.g., four as shown in FIGS. 13 and 14) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument

FIG. 13 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys, or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on the force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on the torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71 or in the wrist at the distal portion of the elongated shaft 71. During a surgical procedure, such as a laparoscopic, endoscopic or hybrid procedure, these tendons may be coupled to a distally mounted end effector, such as a wrist, grasper, or scissor. Under such an arrangement, torque exerted on the drive inputs 73 would transfer tension to the tendon, thereby causing the end effector to actuate in some way. In laparoscopy, the tendon may cause a joint to rotate about an axis, thereby causing the end effector to move in one direction or another. Alternatively, the tendon may be connected to one or more jaws of a grasper at the distal end of the elongated shaft 71, where the tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from the tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but also exhibits more limited bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 13, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopy procedure.

FIG. 14 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 13.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

E. Navigation and Control

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 15:
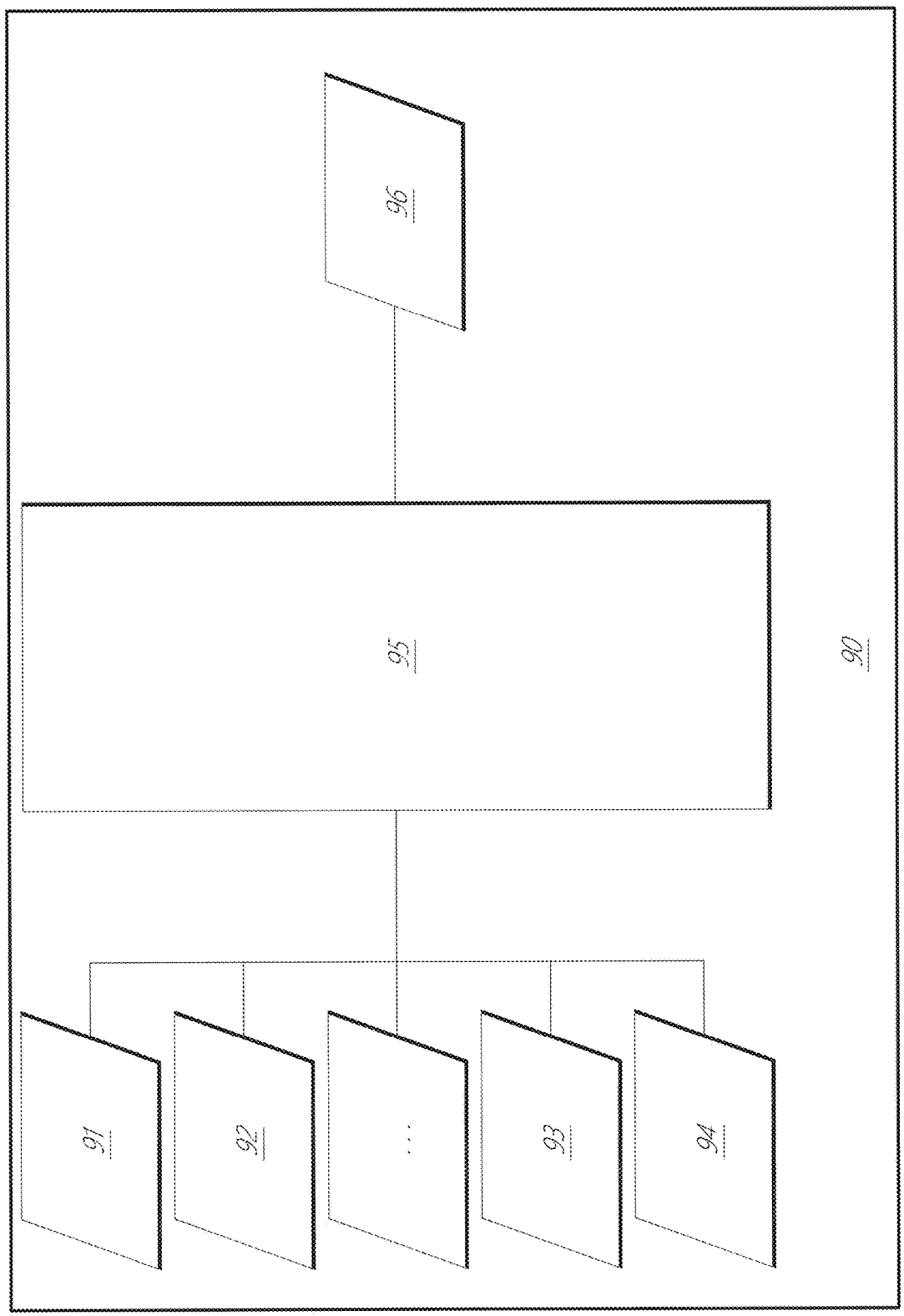
FIG. 15 depicts a block diagram illustrating a localization system that estimates a location of one or more elements of the robotic systems of FIGS. 1-10, such as the location of the instrument of FIGS. 13-14, in accordance to an example embodiment.

FIG. 15 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-10, etc.

As shown in FIG. 15, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be accomplished through the use of the collection of low dose computed tomography (CT) scans. Preoperative CT scans are reconstructed into three-dimensional images, which are visualized, e.g. as "slices" of a cutaway view of the patient's internal anatomy. When analyzed in the aggregate, image-based models for anatomical cavities, spaces, and structures of the patient's anatomy, such as a patient lung network, may be generated. Techniques such as center-line geometry may be determined and approximated from the CT images to develop a three-dimensional volume of the patient's anatomy, referred to model data 91 (also referred to as "preoperative model data" when generated using only preoperative CT scans). In some embodiments, the preoperative model data 91 may include data from, e.g., fluoroscopy, magnetic resonance imaging (MRI), ultrasound imaging, and/or x-rays. The use of center-line geometry is discussed in U.S. patent application Ser. No. 14/523,760, the contents of which are herein incorporated in its entirety. Network topological models may also be derived from the CT images, and are particularly appropriate for bronchoscopy.

In some embodiments, the instrument may be equipped with a camera to provide vision data (or image data) 92. The localization module 95 may process the vision data 92 to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 95. For example, although not shown in FIG. 15, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed, and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

II. Navigation of Luminal Networks

The various robotic systems discussed above can be employed to perform a variety of medical procedures, such as endoscopic and laparoscopy procedures. During certain procedures, a medical instrument, such as a robotically-controlled medical instrument, is inserted into a patient's body. Within the patient's body, the instrument may be positioned within a luminal network of the patient. As used herein, the term "luminal network" refers to any cavity structure within the body, whether comprising a plurality of lumens or branches (e.g., a plurality of branched lumens, as in the lung or blood vessels) or a single lumen or branch (e.g., within the gastrointestinal tract). During the procedure, the instrument may be moved (e.g., navigated, guided, driven, etc.) through the luminal network to one or more areas of interest. Movement of the instrument through the system may be aided by the navigation or localization system 90 discussed above, which can provide positional information about the instrument to a physician controlling the robotic system.

Figure 16:
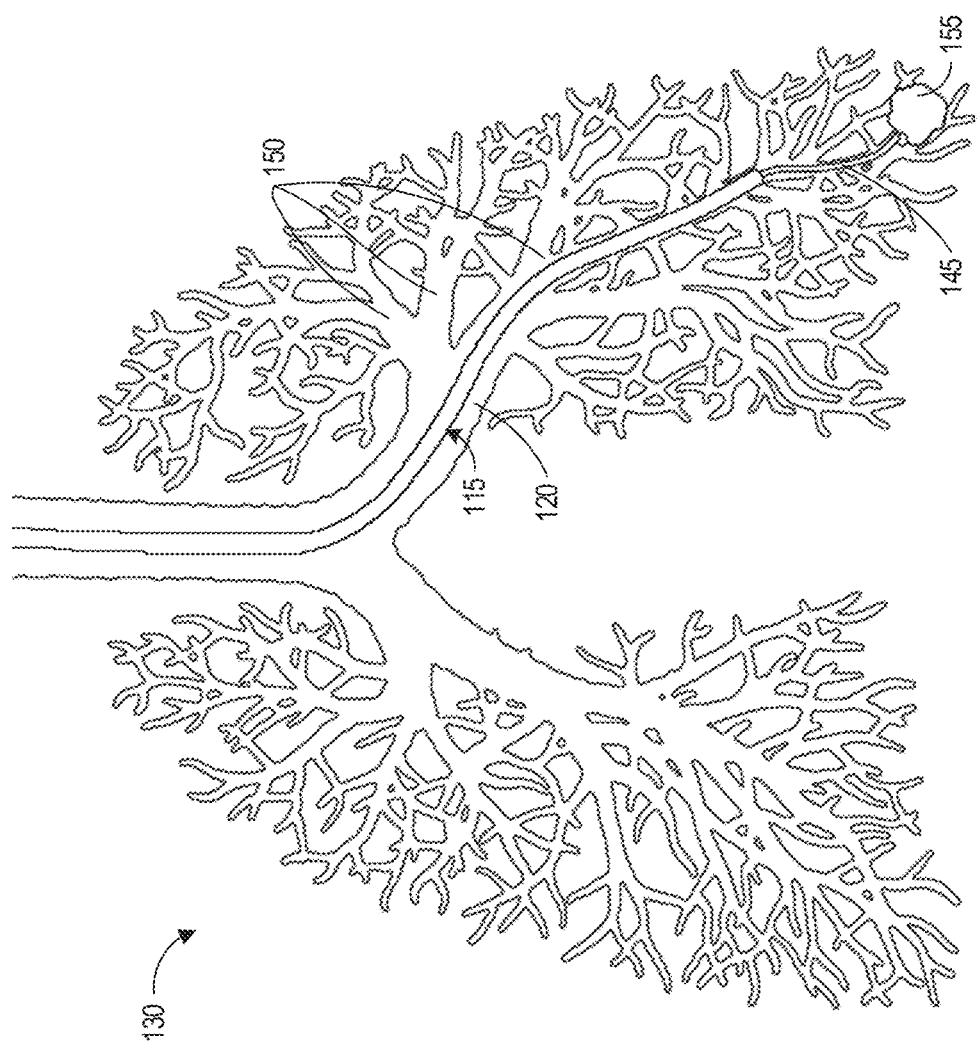
FIG. 16 illustrates an example of an instrument navigating a luminal network.

FIG. 16 illustrates an example luminal network 130 of a patient. In the illustrated embodiment, the luminal network 130 is a bronchial network of airways 150 (i.e., lumens, branches) of the patient's lung. Although the illustrated luminal network 130 is a bronchial network of airways within the patient's lung, this disclosure is not limited to only the illustrated example. The robotic systems and methods described herein may be used to navigate any type of luminal network, such as bronchial networks, renal networks, cardiovascular networks (e.g., arteries and veins), gastrointestinal tracts, urinary tracts, etc.

As illustrated, the luminal network 130 comprises a plurality of airways 150 that are arranged in a branched structure. In general, the luminal network 130 comprises a three-dimensional structure. For ease of illustration, FIG. 16 represents the luminal network 130 as a two-dimensional structure. This should not be construed to limit the present disclosure to two-dimensional luminal networks in any way.

FIG. 16 also illustrates an example of a medical instrument positioned within the luminal network 130. The medical instrument is navigated through the luminal network 130 towards an area of interest (e.g., nodule 155) for diagnosis and/or treatment. In the illustrated example, the nodule 155 is located at the periphery of the airways 150, although the area(s) of interest can be positioned anywhere within the luminal network 130 depending on the patient and procedure.

In the illustrated example, the medical instrument comprises an endoscope 115. The endoscope 115 can include a sheath 120 and a leader 145. In some embodiments, the sheath 120 and the leader 145 may be arranged in a telescopic manner. For example, the leader 145 may be slidably positioned inside a working channel of the sheath 120. The sheath 120 may have a first diameter, and its distal end may not be able to be positioned through the smaller-diameter airways 150 around the nodule 155. Accordingly, the leader 145 may be configured to extend from the working channel of the sheath 120 the remaining distance to the nodule 155. The leader 145 may have a lumen through which instruments, for example biopsy needles, cytology brushes, and/or tissue sampling forceps, can be passed to the target tissue site of the nodule 155. In such implementations, both the distal end of the sheath 120 and the distal end of the leader 145 can be provided with EM instrument sensors (e.g., EM instrument sensors 305 in FIG. 18) for tracking their position within the airways 150. This telescopic arrangement of the sheath 120 and the leader 145 may allow for a thinner design of the endoscope 115 and may improve a bend radius of the endoscope 115 while providing a structural support via the sheath 120.

In other embodiments, the overall diameter of the endoscope 115 may be small enough to reach the periphery without the telescopic arrangement, or may be small enough to get close to the periphery (e.g., within about 2.5-3 cm) to deploy medical instruments through a non-steerable catheter. The medical instruments deployed through the endoscope 115 may be equipped with EM instrument sensors (e.g., EM instrument sensors 305 in FIG. 18), and the image-based airway analysis and mapping techniques described below can be applied to such medical instruments.

As shown, to reach the nodule 155, the instrument (e.g., endoscope 115) must be navigated or guided through the airways 150 of the luminal network. An operator (such as a physician) can control the robotic system to navigate the instrument to the nodule 155. The operator may provide inputs for controlling the robotic system.

Figure 17:
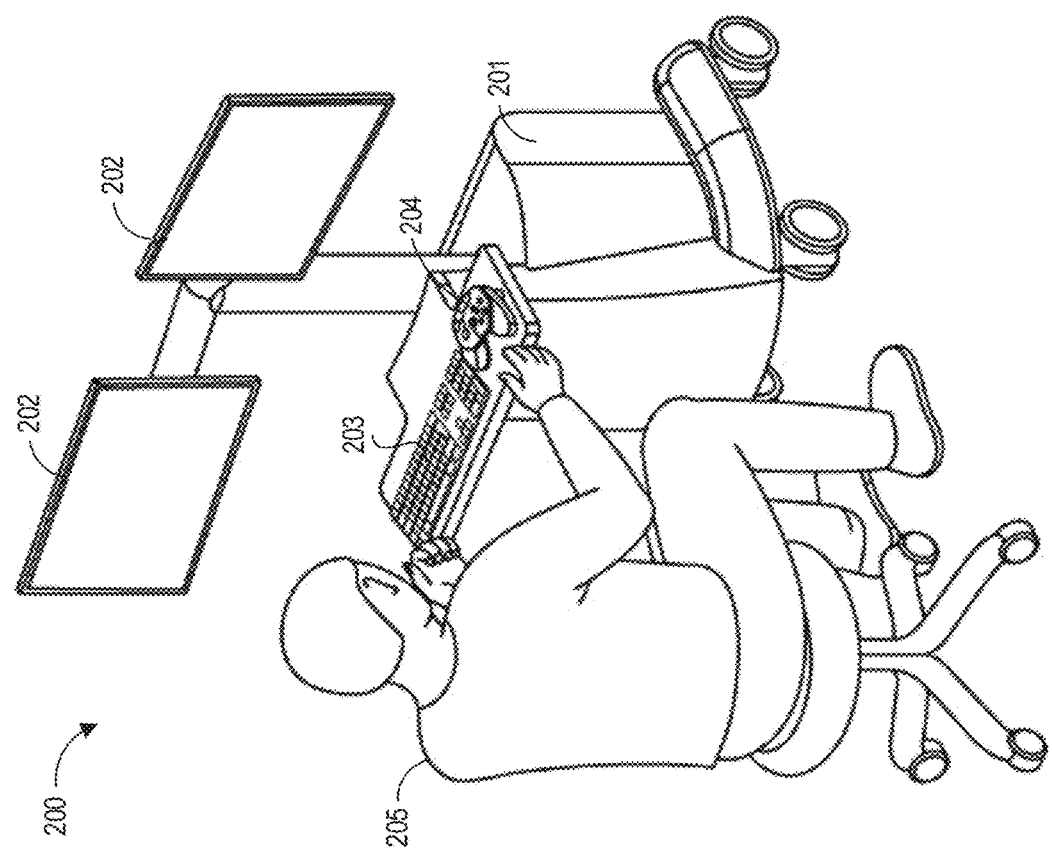
FIG. 17 illustrates an example command console for a robotically-controlled surgical system.

FIG. 17 illustrates an example command console 200 that can be used with some implementations of the robotic systems described herein. The operator may provide the inputs for controlling the robotic system, for example, to navigate or guide the instrument to an area of interest such as nodule 155, via the command console 200. The command console 200 may be embodied in a wide variety of arrangements or configurations. In the illustrated example, the command console 200 includes a console base 201, displays 202 (e.g., monitors), and one or more control modules (e.g., keyboard 203 and joystick 204). A user 205 (e.g., physician or other operator) can remotely control the medical robotic system (e.g., the systems described with reference to FIGS. 1-15) from an ergonomic position using the command console 200.

The displays 202 may include electronic monitors (e.g., LCD displays, LED displays, touch-sensitive displays), virtual reality viewing devices (e.g., goggles or glasses), and/or other display devices. In some embodiments, one or more of the displays 202 displays position information about the instrument, for example, as determined by the localization system 90 (FIG. 15). In some embodiments, one or more of the displays 202 displays a preoperative model of the patient's luminal network 130. The positional information can be overlaid on the preoperative model. The displays 202 can also display image information received from a camera or another sensing device positioned on the instrument within the luminal network 130. In some embodiments, a model or representation of the instrument is displayed with the preoperative model to help indicate a status of a surgical or medical procedure.

In some embodiments, the console base 201 includes a central processing unit (e.g., CPU or processor), a memory unit (e.g., computer-readable memory), a data bus, and associated data communication ports that are responsible for interpreting and processing signals such as camera imagery and tracking sensor data, e.g., from a medical instrument positioned within a luminal network of a patient.

The console base 201 may also process commands and instructions provided by the user 205 through control modules 203, 204. In addition to the keyboard 203 and joystick 204 shown in FIG. 17, the control modules may include other devices, such as computer mice, trackpads, trackballs, control pads, controllers such as handheld remote controllers, and sensors (e.g., motion sensors or cameras) that capture hand gestures and finger gestures. A controller can include a set of user inputs (e.g., buttons, joysticks, directional pads, etc.) mapped to an operation of the instrument (e.g., articulation, driving, water irrigation, etc.). Using the control modules 203, 204 of the command console 200, the user 205 may navigate an instrument through the luminal network 130.

Figure 18:
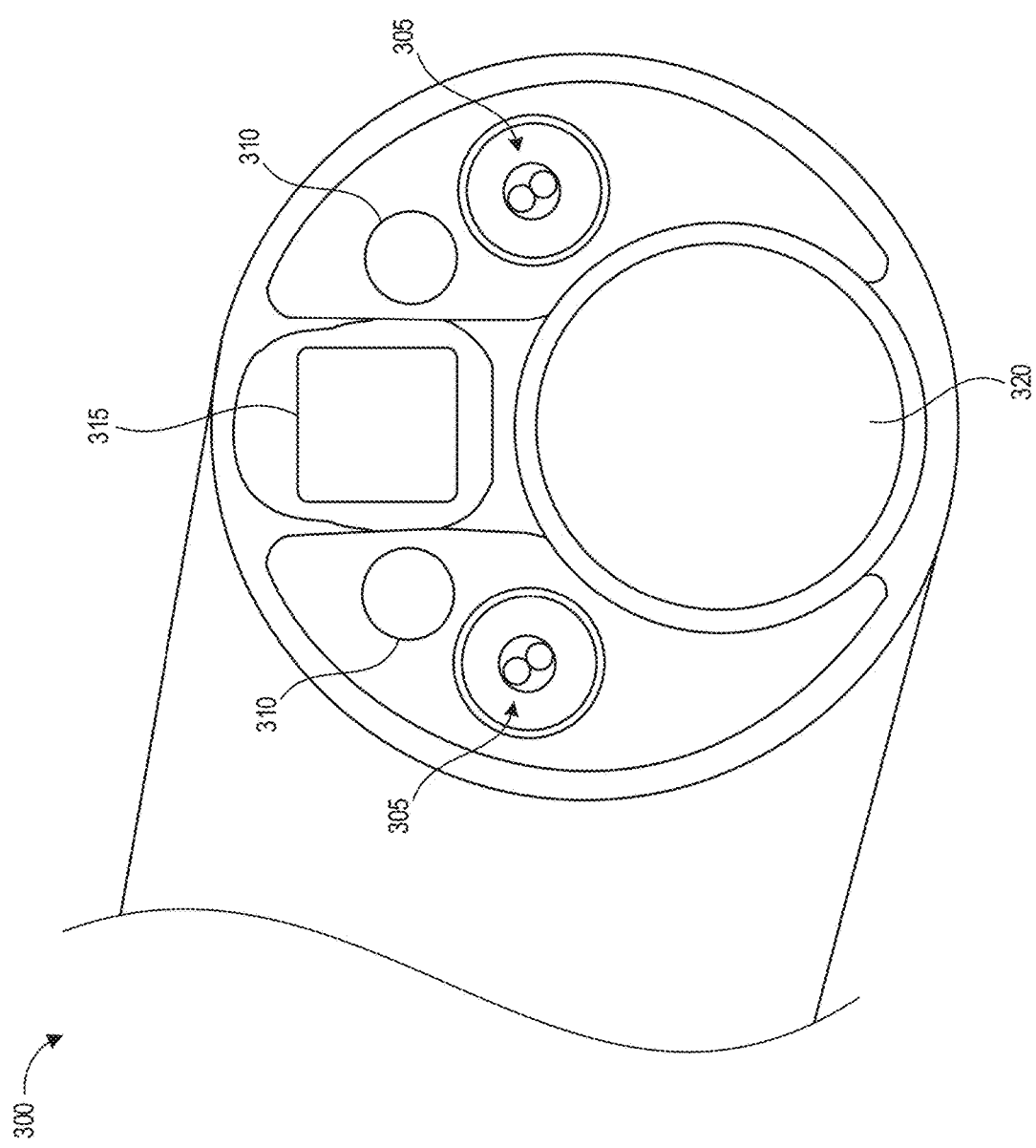
FIG. 18 illustrates a distal end of an embodiment of a medical instrument.

FIG. 18 illustrates a detail view of a distal end of an example medical instrument 300. The medical instrument 300 may be representative of the endoscope 115 or steerable catheter 145 of FIG. 16. The medical instrument 300 may be representative of any medical instrument described throughout the disclosure, such as the endoscope 13 of FIG. 1, the ureteroscope 32 of FIG. 3, the laparoscope 59 of FIG. 9, etc. In FIG. 18, the distal end of the instrument 300 includes an imaging device 315, illumination sources 310, and ends of EM sensor coils 305, which form an EM instrument sensor. The distal end further includes an opening to a working channel 320 of the instrument 300 through which surgical instruments, such as biopsy needles, cytology brushes, forceps, etc., may be inserted along the instrument shaft, allowing access to the area near the instrument tip.

EM coils 305 located on the distal end of the instrument 300 may be used with an EM tracking system to detect the position and orientation of the distal end of the instrument 300 while it is positioned within a luminal network. In some embodiments, the coils 305 may be angled to provide sensitivity to EM fields along different axes, giving the disclosed navigational systems the ability to measure a full 6 degrees of freedom (DoF): three positional DoF and three angular DoF. In other embodiments, only a single coil 305 may be disposed on or within the distal end with its axis oriented along the instrument shaft. Due to the rotational symmetry of such a system, it may be insensitive to roll about its axis, so only five degrees of freedom may be detected in such an implementation. Alternatively or additionally, other types of position sensors may be employed.

The illumination sources 310 provide light to illuminate a portion of an anatomical space. The illumination sources 310 can each be one or more light-emitting devices configured to emit light at a selected wavelength or range of wavelengths. The wavelengths can be any suitable wavelength, for example, visible spectrum light, infrared light, x-ray (e.g., for fluoroscopy), to name a few examples. In some embodiments, the illumination sources 310 can include light-emitting diodes (LEDs) located at the distal end of the instrument 300. In some embodiments, the illumination sources 310 can include one or more fiber optic fibers extending through the length of the endoscope to transmit light through the distal end from a remote light source, for example, an x-ray generator. Where the distal end includes multiple illumination sources 310, these can each be configured to emit the same or different wavelengths of light as one another.

The imaging device 315 can include any photosensitive substrate or structure configured to convert energy representing received light into electric signals, for example, a charge-coupled device (CCD) or complementary metal-oxide semiconductor (CMOS) image sensor. Some examples of the imaging device 315 can include one or more optical fibers, for example, a fiber optic bundle, configured to transmit light representing an image from the distal end 300 of the endoscope to an eyepiece and/or image sensor near the proximal end of the endoscope. The imaging device 315 can additionally include one or more lenses and/or wavelength pass or cutoff filters as required for various optical designs. The light emitted from the illumination sources 310 allows the imaging device 315 to capture images of the interior of a patient's luminal network. These images can then be transmitted as individual frames or series of successive frames (e.g., a video) to a computer system such as command console 200. As mentioned above and as will be described in greater detail below, the images captured by the imaging device 315 (e.g., vision data 92 of FIG. 15) can be utilized by the navigation or localization system 95 to determine or estimate the position of the instrument (e.g., the position of the distal tip of the instrument 300) within a luminal network.

III. Image-Based Airway Analysis and Mapping

Embodiments of the disclosure relate to systems and techniques for image-based airway analysis and mapping. As used herein, image-based airway analysis may refer to identifying within an image one or more airways associated with one or more branches of a luminal network and determining branching information indicative of how the current airway in which the image is captured branches into the detected "child" airways. For example, an image-based airway analysis system may capture an image of an interior of a luminal network using an imaging device positioned on an instrument within the luminal network, and the image-based airway analysis system may analyze the image to identify one or more airways shown in the image. As used herein, image-based airway mapping may refer to mapping the airways identified in the image to corresponding airways or branches of the luminal network indicated by, for example, the preoperative model data. For example, an image-based airway mapping system may be configured to identify which airways or branches of a given luminal network correspond to the airways or branches identified in the captured images. These systems and techniques may be used to determine or estimate the position of an instrument within the luminal network. In certain implementations, these systems and techniques may be used in conjunction with various other navigation and localization modalities (e.g., as described above with reference to FIG. 15).

A. Overview of Image-Based Airway Analysis and Mapping

The ability to navigate inside a luminal network may be a feature of the robotically-controlled surgical systems described herein. As used herein, navigation may refer to locating or determining the position of an instrument within a luminal network. The determined position may be used to help guide the instrument to one or more particular areas of interest within the luminal network. In some embodiments, the robotically-controlled surgical systems utilize one or more independent sensing modalities to provide intraoperative navigation for the instrument. As shown in FIG. 15, the independent sensing modalities may provide position data (e.g., EM data 93), vision data 92, and/or robotic command and kinematics data 94. These independent sensing modalities may include estimation modules configured to provide independent estimates of position. The independent estimates can then be combined into one navigation output, for example, using localization module 95, which can be used by the system or displayed to the user. Image-based airway analysis and mapping may provide an independent sensing modality, based on vision data 92, that can provide an independent estimate of position. In particular, in some instances image-based airway analysis and mapping provides a combination of a sensing modality and a state/position estimation module that estimates which lumen or branch of a luminal network an imaging device of the instrument is located based on one or more images captured by the imaging device. In some embodiments, the estimate provided by image-based airway analysis and mapping may be used alone or with other position estimates to determine a final position estimate that can be used by the system or displayed to the user. In some embodiments, the image-based airway analysis and mapping systems and methods described herein may base its estimate on prior position estimates determined using a plurality sensing modalities.

Figure 19:
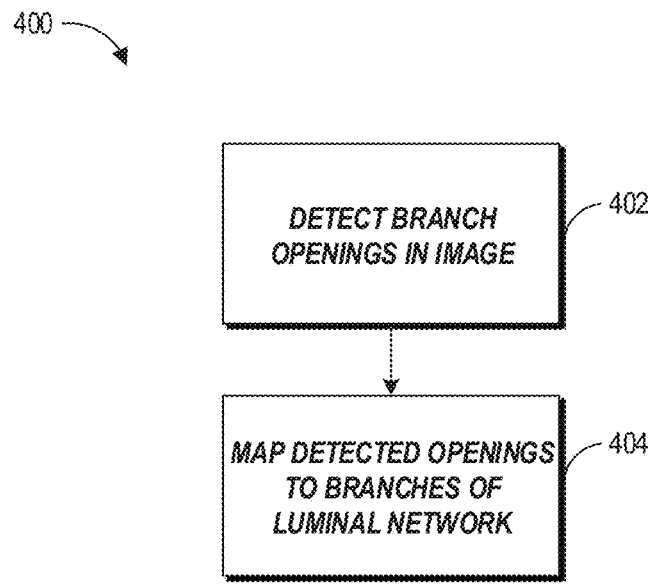
FIG. 19 depicts a flowchart illustrating an example method for image-based airway analysis and mapping.

FIG. 19 illustrates an example method 400 for image-based airway analysis and mapping. The method 400 may be implemented in various robotically-controlled surgical systems as described herein. The method 400 may include two steps or blocks: detecting airways in an image (block 402) and mapping the detected airways to corresponding airways (e.g., indicated by the preoperative model data) of the luminal network (block 404).

At block 402, the method 400 detects one or more airways within an image. As noted above, during a medical procedure, an instrument may be positioned within a luminal network (see FIG. 16). As shown in FIG. 18, the instrument may include an imaging device 315 (such as a camera) positioned thereon. The imaging device 315 may capture images of the interior of the luminal network. For example, at a particular instant, the imaging device 315 may capture an image of the interior of the particular airway of the luminal network in which the instrument is currently positioned. At block 402, the method 400 can analyze the image to detect one or more airways within the image. For example, an airway detected within the image may be a set of pixels that satisfy an airway detection condition (e.g., having a pixel intensity greater than a threshold value). The detected airway may be the current airway in which the image is captured by the imaging device 315 and/or one or more child airways (e.g., subsequent branches of the luminal network) of the current airway. Block 402 may involve image analysis that processes an image to determine the number and location of the airways shown in the image. In certain implementations, if the image is determined to contain one or more airways, various features of the airways may also be determined. Such features may include determining a shape or contour of the detected airways and/or determining a centroid of the detected airways.

At block 404, the method 400 maps the one or more detected airways to specific airways of the luminal network. At block 404, the method 400 determines which airways of the luminal network branches into which other subsequent airways of the luminal network. For example, based on certain preoperative model data (e.g., CT data), the system may be aware of the airways that are expected to be captured in a given image (e.g., based on the current location of the imaging device 315). Upon detecting one or more airways in the image at block 402, the method 400 may map the detected airways to the expected airways based on the preoperative model data.

By mapping the airways detected in the camera image to corresponding expected airways in the luminal network, the method 400 may provide an estimate of position for the instrument. For example, using the method 400, the system or the instrument can identify which airways the instrument "sees" and use this information to estimate, within the luminal network, the airway in which the instrument is currently located and the airway that the instrument is about to enter.

B. Image-Based Airway Analysis

Figure 20:
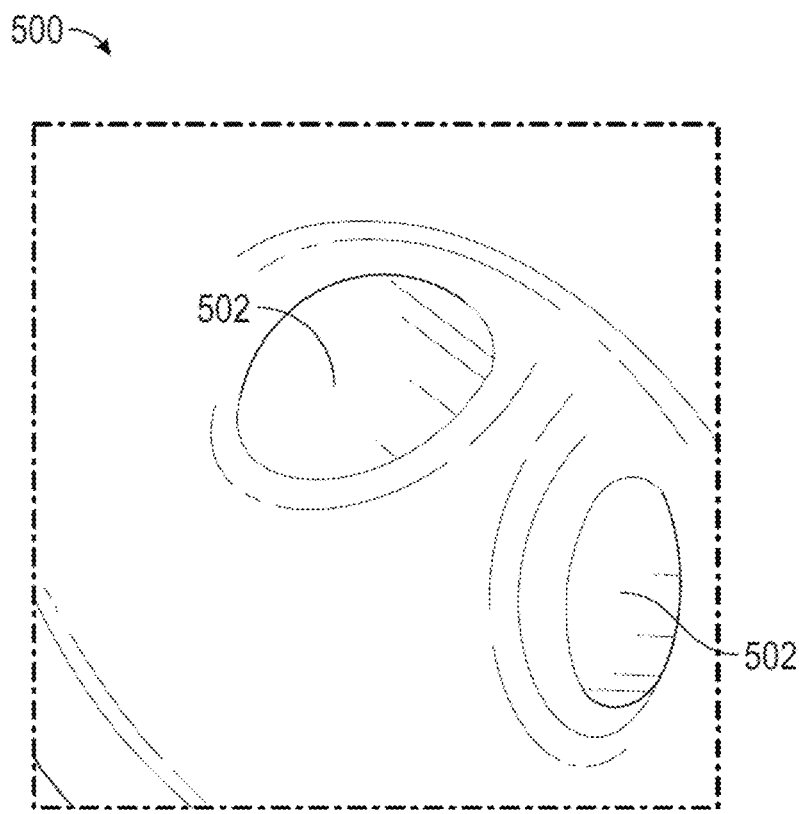
FIG. 20 illustrates an example image of an interior of a branch of a luminal network.

Image-based airway analysis may include analyzing an image captured by the imaging device 315 of an instrument positioned within a luminal network to detect one or more airways in the image. FIG. 20 provides an example image 500 of an interior of a branch of a luminal network. In the illustrated example, the image 500 is an interior image of an airway of a lung, although the image 500 may be representative of any type of luminal network. Two subsequent airways 502 are shown in the image 500. The airways 502 are connected to the current airway from which the image is captured.

Image-based airway analysis can include a method whereby a computer system can recognize the airways 502 computationally. In some cases, the image 500 includes two classes of pixels: (1) pixels representing walls of the luminal network (e.g., tissue), and (2) pixels representing airways (e.g., airway openings). According to certain embodiments, the image-based airway analysis can systematically detect these two classes of pixels to identify and detect airways within an image. For example, the airways 502 may be detected by classifying the pixels into these two classes based on the pixel intensity. Image analysis and detection methods based on pixel intensity are described in greater detail in U.S. patent application Ser. No. 15/783,903, the contents of which are herein incorporated in its entirety.

C. Image-Based Airway Mapping

Image-based airway mapping techniques described herein may be used to determine which branches of the luminal network are associated with the detected branches or airways. That is, image-based airway mapping can determine which subsequent branches of the luminal network are connected to the current branch from which the image is captured. By mapping the detected airways to branches of the luminal network, the position of the instrument within the luminal network can be determined. Further, an estimate or prediction of which branch the instrument will be moved into can also be obtained.

In some embodiments, detected airways can be mapped to branches of the luminal network by comparing features of the detected airways to features of the branches of the luminal network. The features of the detected airways may be determined through image analysis as described above. The features of the branches of the luminal network can be determined from a model of the luminal network, such as a preoperative model of the luminal network. Further, in certain embodiments, mapping detected airways to branches of the luminal network can be based on a current position estimate of the instrument within the luminal network. The current position estimate can be determined based on various sensing modalities as described above with reference to FIG. 15. Mapping detected airways to branches of the luminal network based on a current position estimate can improve the efficiency, speed, and/or accuracy of the mapping process. For example, given a current position estimate, features of the detected airways can be compared to features of expected subsequent branches. This may minimize the computational load required to perform the mapping and improve mapping speed.

Figure 21:
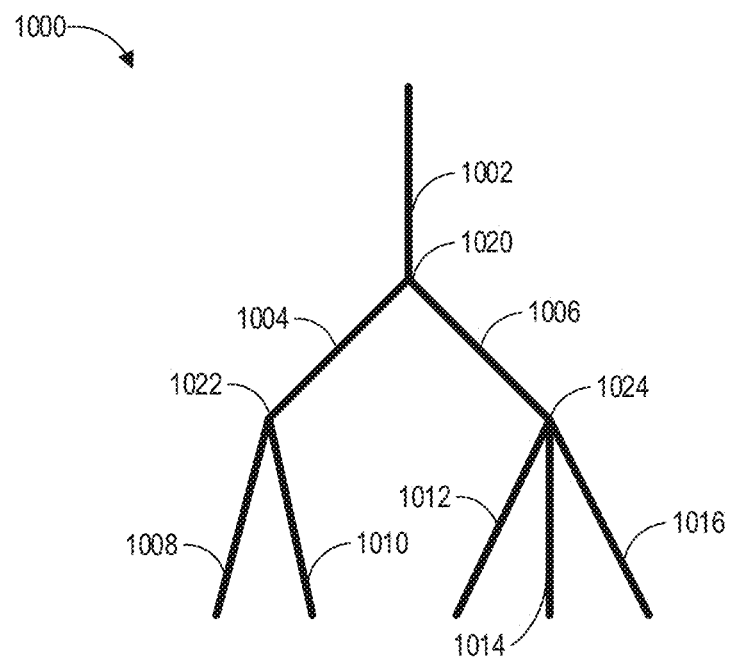
FIG. 21 illustrates a simplified view of a luminal network.

FIG. 21 illustrates a simplified representation of a luminal network 1000. The luminal network 1000 comprises a plurality of branches (e.g., lumens, segments, airways, etc.) 1002, 1004, 1006, 1008, 1010, 1012, 1014, 1016. The luminal network 1000 also comprises bifurcations 1020, 1022 and trifurcation 1024 connecting various branches to each other. In the example of FIG. 21, the branches 1004, 1006 are in the same generation, and the branches 1008, 1010, 1012, 1014, 1016 are in the same generation. In some embodiments, the luminal network 1000 may represent a portion of a bronchial network of a lung, and the branches may represent airways. Although many example embodiments of the present disclosure are described with reference to airways in a bronchial network, the embodiments are not limited as such and may be extended to other types of branches in other types of luminal networks.

The luminal network 1000 may be represented by a model. In some embodiments, the model is determined preoperatively. For example, preoperative model data 91 (i.e., information about the preoperative model) may be stored and made available to the navigation and localization system 90 (FIG. 15). In other embodiments, at least a portion of the model is determined intraoperatively. As will be described below as an example, image-based airway mapping can be configured to map the detected branches to the branches of the luminal network 1000 generated based on the preoperative model data 91.

D. Potential Challenges with Image-Based Airway Detection

Figure 22:
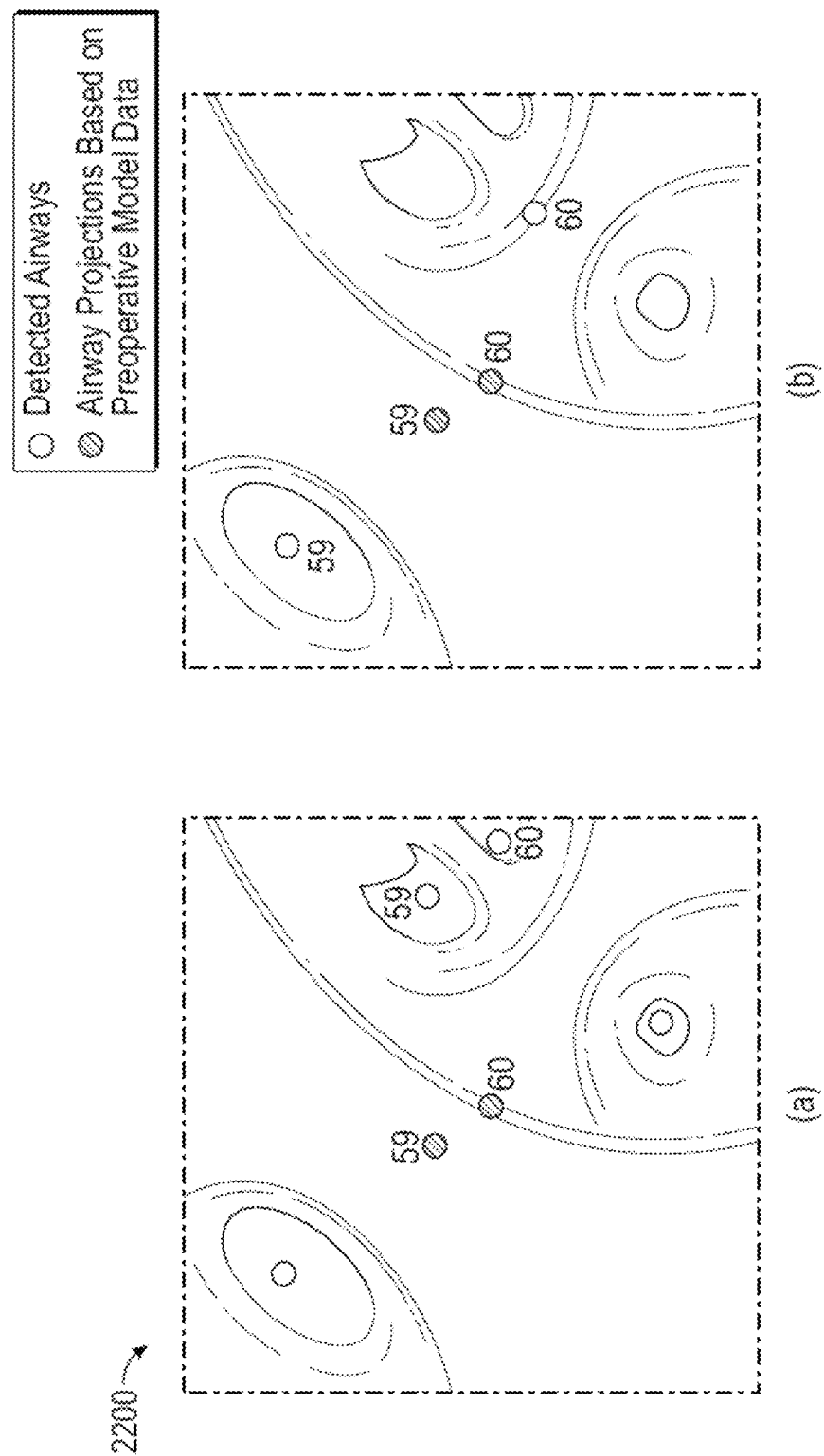
FIG. 22 illustrates two different example airway detection results.

In some cases, the images captured by a bronchoscopic camera may contain airways from different generations. In such cases, the number of airways detected by the image-based airway detection methods described herein may be incorrect. For example, FIG. 22 shows image 2200(*a*) (left) and image 2200(*b*) (right) captured in the branch 1002 of the luminal network 1000 of FIG. 21. In the example of FIG. 22, airway projections have been added to the images 2200(*a*), 2200(*b*) to indicate the number and locations of the branches expected to be seen from the current camera location.

The image-based airway detection method performed on the image 2200(*a*) has resulted in four detected airways as shown in the image 2200(*a*). Such a result may cause the system to determine that the current airway branches into the four detected branches. However, as indicated by the hierarchical structure of FIG. 21, such a determination would be incorrect. The preoperative model data (e.g., hierarchical structure of the luminal network 1000 illustrated in FIG. 21) indicates (correctly, and in a manner consistent with the preoperative model data) that the branch 1002 from which the image 2200(*a*) is captured is expected to branch into two branches (i.e. branches 1004 and 1006), and not four branches as detected in the image 2200(*a*). While the image 2200(*a*) clearly shows four airways, three of the airways pictured at the bottom right corner of the image 2200(*a*) are "grandchildren" (i.e. branches 1012, 1014, 1016) of the current branch 1002 that branched out from the branch 1006 that is immediately subsequent to the current branch 1002 (i.e. "child" of the current branch 1002).

Thus, in some embodiments, by utilizing the preoperative model data indicative of the number (i.e. count and/or location) of airways to be present in a given image, the airway analysis and mapping systems and methods of the present disclosure can detect the correct number of airways, as illustrated in the image 2200(*b*).

E. Airway Analysis

Figure 23A:
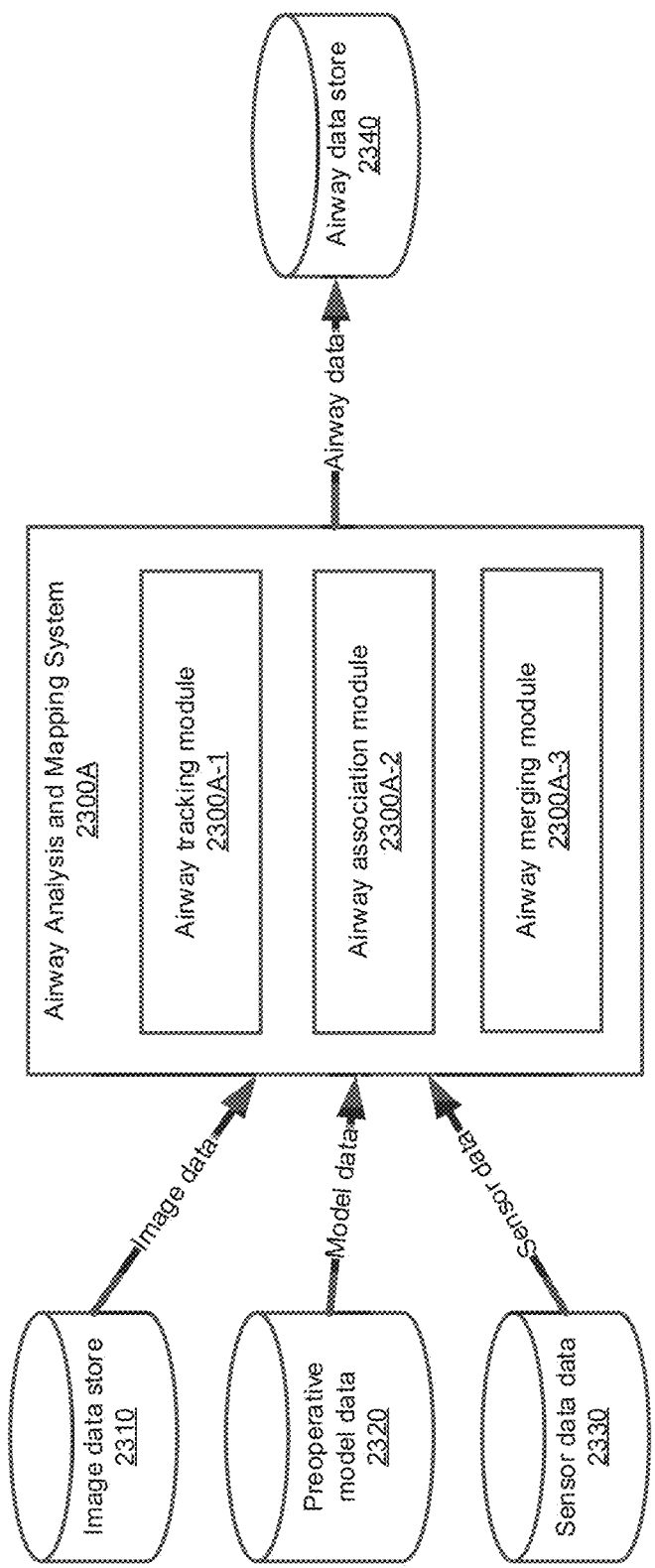
FIG. 23A illustrates an airway analysis and mapping system according to example embodiments.

FIG. 23A illustrates an example airway analysis and mapping system 2300A. As shown, the airway analysis and mapping system 2300A includes an airway tracking module 2300A-1, an airway association module 2300A-2, and an airway merging module 2300A-3. The airway analysis and mapping system 2300A receives as input (i) image data (e.g., image captured using an imaging device) from an image data store 2310 (*ii*) model data (e.g., preoperative model data such as fluoroscopy data, MRI data, ultrasound imaging data, x-ray data, and the like) from a preoperative model data store 2320, (iii) sensor data (e.g., EM data, vision data, robot data, shape sensing fiber data, and the like) from a sensor data store 2330 and outputs airway data (e.g., location, size, and center of identified or merged airways, mapping between identified or merged airways and preoperative model data, and the like) to the airway data store 2340. The airway tracking module 2300A-1 identifies the airway(s) in each image in the image data. The airway association module 2300A-2 associates the airway(s)s in current image with the airway(s) in prior images. The airway merging module 2300A-3 determines whether two or more airways should be merged based on their relationship, for example, using the sensor data and the preoperative model data. The process of identifying, associating, and merging airways according to various embodiments is described in greater detail below with reference to FIGS. 23B, 24, and 25.

Figure 23B:
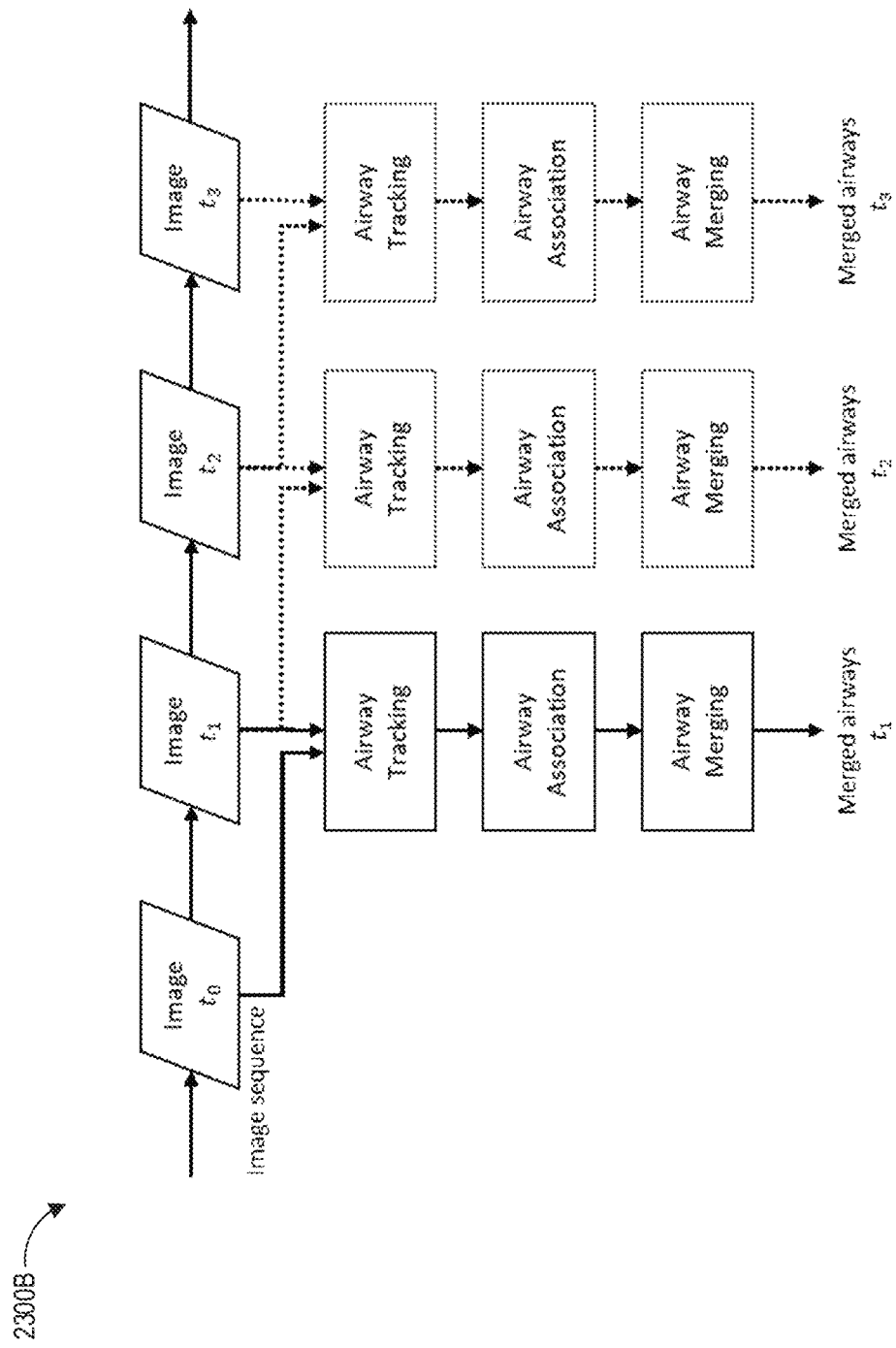
FIG. 23B illustrates the temporal context in which the image-based airway analysis according to example embodiments is performed.

FIG. 23B illustrates the temporal context in which the image-based airway analysis according to example embodiments is performed. For simplicity, one or more steps are described as being performed by a system (e.g., the airway analysis and mapping system 2300A).

As shown, a series of images (i.e., images $t_0$, $t_1$, ... ) are captured by an imaging device on a medical instrument navigating the luminal network of a patient, and images captured at different times (e.g., $t_0$ and $t_1$) undergo airway tracking, airway association, and airway merging. At a high level, this process of performing airway tracking, airway association, and airway merging analyzes a stream of images captured by the imaging device to compare locations of currently detected airways with estimated locations of airways detected in prior images and then determines a relationship between the airways detected in the current and prior images to determine whether the airways should be merged. The stream of images, or data derived therefrom, such as airway location information, may be stored by the system to perform the analysis. Temporal airway tracking, airway association, and airway merging are now described in greater detail.

Figure 24:
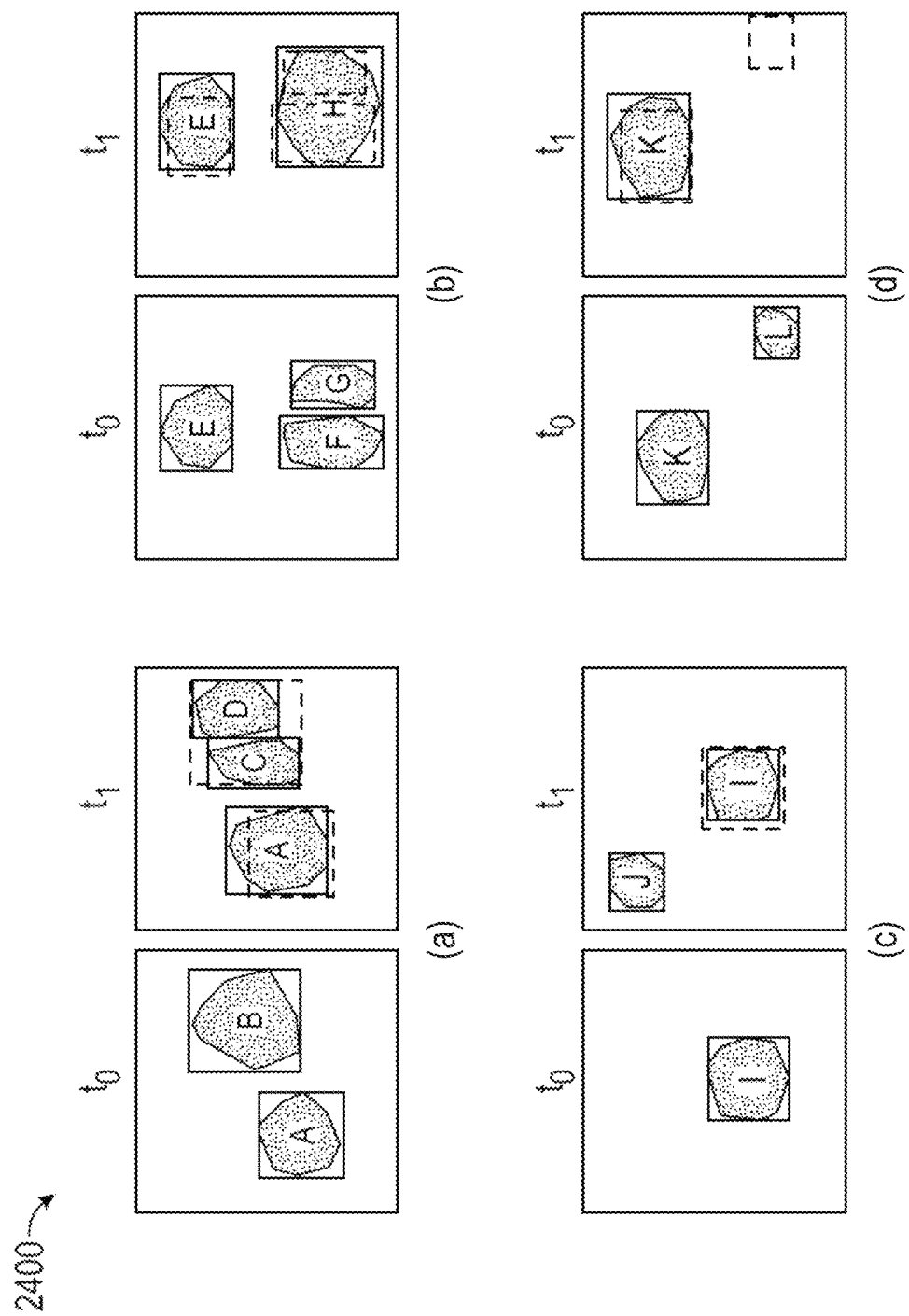
FIG. 24 illustrates the spatial nature of the image-based airway analysis according to example embodiments.

FIG. 24 illustrates the spatial nature of the image-based airway analysis according to example embodiments. As shown, the airways in the previous and current images can exhibit a variety of different types of spatial relationship (e.g., one-to-one, one-to-many, many-to-one, zero-to-one, and one-to-zero). These examples are described in greater detail below in connection with Airway Association.

E.1. Temporal Airway Tracking

At a high level, image-based temporal tracking involves estimating the status (e.g., locations and sizes) of the airways in a current image relative to the status of the airways in a previous image. As shown in FIG. 23B, the airway tracking process receives as input a current image at $t_1$ and airway information derived from a prior image, say prior image at $t_0$. Based on the input, the system can determine an expected location of the prior airway relative to the current image and determine the current locations of the airways detected in the current image.

Figure 25:
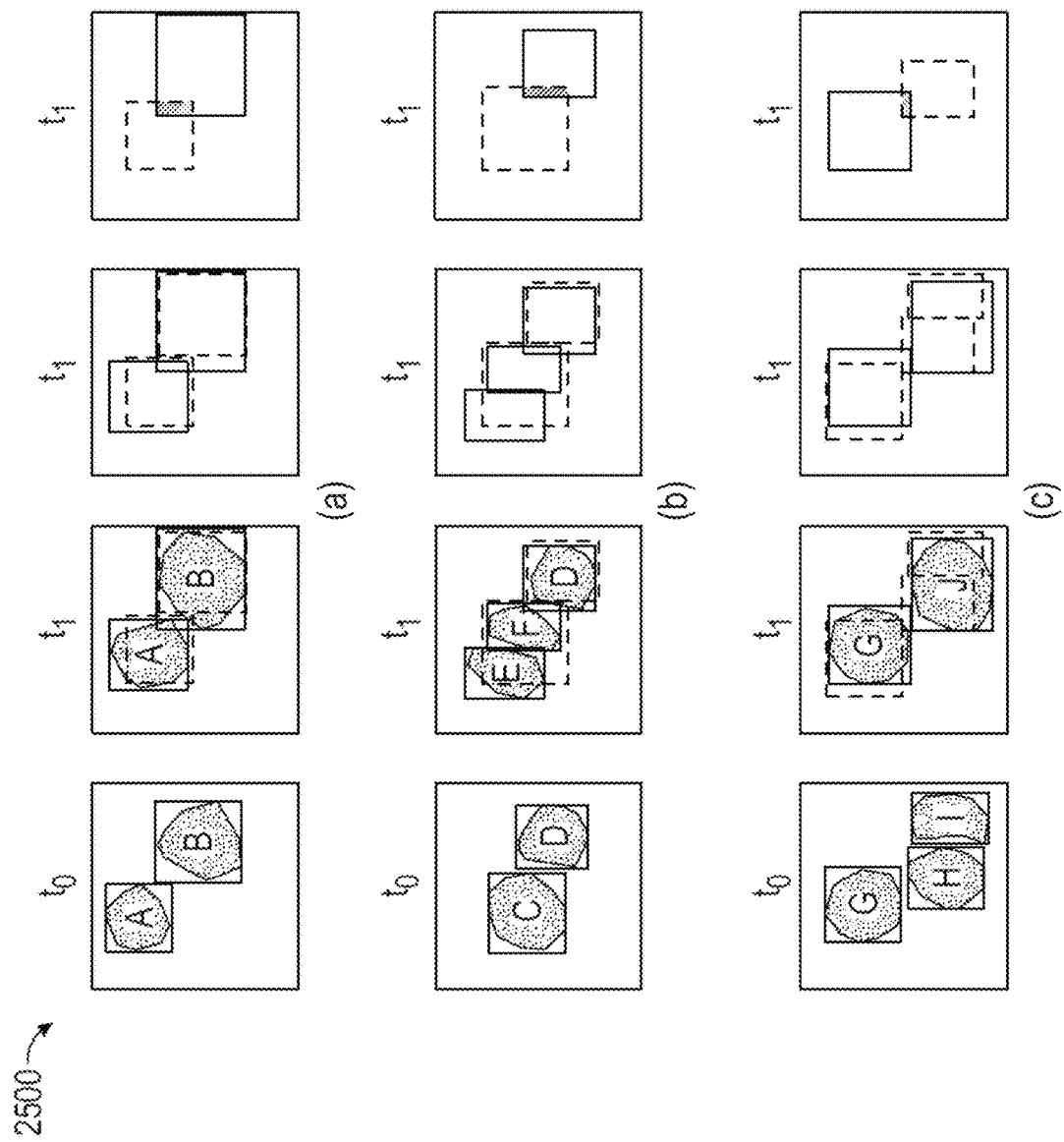
FIG. 25 illustrates additional example relationships exhibited by detected airways in two consecutive images.

This process of identifying current locations of airways and expected locations of past airways is shown in FIG. 25. For example, in the first row, at time $t_0$ locations of airways A and B are identified, as represented in solid boxes. At time $t_1$ the temporal airway tracking receives as input the detected locations of A and B and may optionally estimate an updated location for these airways based on, for example, movement of the scope using, as way of example and not limitation, optical flow techniques. Examples of optical flow techniques may include motion detection, object segmentation calculations, luminance, motion compensated encoding, stereo disparity measurement, etc. The estimated locations of prior airways at time $t_1$ are shown in dashed boxes. The temporal airway tracking also analyzes the current image to detect locations of airways detectable in the current image at time $t_1$. The current locations of the detected airways at the image at time $t_1$ is shown in solid boxes. FIG. 25 is described in greater detail below in connection with Airway Association.

Accordingly, the airway tracking process determines, for a current time, the estimated locations of prior airways relative to the current image and the locations of airways currently detected in the image data for the current time.

E.2. Airway Association Based on Temporal and Spatial Analysis

In general, Airway Association, as executed by the system, may create a relationship between the airways detected in prior images and the airways detected in the current images. Airway Association creates these relationships based on the locations of the prior airways and the locations of the detected airways as may be determined by the airway tracking. A relationship may represent cases where a prior airway is now detected as two separate airways. Such situations that may cause an airway to be depicted as two different airways include, but not be limited to: detecting airways visible through another airway (e.g., descendent airways); and detecting a transition where an airway initially appears as a single airway but then become apparent that the single airway is actually multiple airways located in close proximity with each other. Further, in some cases, an airway that is not originally part of a prior image may become visible and the Airway Association may take actions to avoid relating that new airway with prior airways.

FIG. 24 illustrates examples of the type of relationship that can be exhibited by the airways in the previous and current images. As shown in FIG. 24, example relationships may include a one-to-one (A→A) association and a one-to-many (B→C,D) association illustrated in 2400($a$); a one-to-one (E→E) association and a many-to-one (F,G→H) association illustrated in 2400($b$); a zero-to-one (none→J) and a one-to-one (I→I) association illustrated in 2400($c$); and a one-to-zero (L→none) and a one-to-one (K→K) association illustrated in 2400($d$). The solid rectangles are bounding boxes encapsulating the detected airways in the current image (e.g., image $t_1$), and the dashed rectangles are bounding boxes encapsulating the detected airways in the previous image (e.g., image $t_0$). Although rectangles and/or bounding boxes are used in some embodiments, such embodiments are not limited as such and may be extended to embodiments using any polygons or other shapes. The associations may be stored by the system as a series of records where the airways are given unique identifiers and may include data that links the unique identifiers for the airways that are associated together.

The system may determine a correspondence between the airways detected in the previous image and the airways detected in the current image by comparing the overlap between the rectangles (or more broadly, the location and shape of the airways) illustrated in FIG. 24. In some embodiments, one or more of the following overlap ratio values (or any combination thereof) may be used to determine whether a given airway corresponds to another airway:

$$O_1(b_1, b_2) = \frac{\Lambda(b_1 \cap b_2)}{\min(\Lambda(b_1), \Lambda(b_2))} \quad (1)$$

$$O_2(b_1, b_2) = \frac{\Lambda(b_1 \cap b_2)}{\max(\Lambda(b_1), \Lambda(b_2))} \quad (2)$$

$$O_3(b_1, b_2) = \frac{\Lambda(b_1 \cap b_2)}{\Lambda(b_1 \cup b_2)} \quad (3)$$

where $\cap$ and $\cup$ denote the intersection and union operators, respectively, between two rectangles $b_1$ and $b_2$. The area (e.g., in pixels) of a rectangle or other bounding shape (which may be calculated by counting the pixels inside the rectangle) is denoted as $\Lambda(\cdot)$. min(p, q) and max(p, q) return the smaller value and larger values from p and q, respectively.

In some embodiments, an association between two rectangles (e.g., one corresponding to one or more airways detected in the previous image, and the other corresponding to one or more airways detected in the current image) is established if the following condition is satisfied:

$$O(b_1, b_2) > \tau \qquad (4)$$

where $\tau$ is a pre-defined threshold and $O(b_1, b_2)$ can be one of the three overlap ratio values ($O_1$, $O_2$ and $O_3$). The three overlap ratio values are examples, and other overlap ratio values may be used instead of or in additional to these overlap ratio values. Although rectangles are used in the example of FIG. 24, in some embodiments, any geometric shapes (e.g., polygons or other shapes) may be used to determine the overlap between the airways. In such embodiments, the overlap between one set of one or more geometric shapes corresponding to one or more airways detected in the current picture and another set of one or more geometric shapes corresponding to one or more airways detected in the previous picture may be calculated. In some embodiments, the geometric shapes used for determining the overlap fully encapsulate the detected airways. In other examples, the geometric shapes do not fully encapsulate the detected airways and partially overlap with the airways. In the earlier example in which the identity of the airways to be merged is known, the system may skip part or all of the geometrical overlap analysis illustrated in FIG. 24.

Although the above has been described as creating associations that are one level deep (e.g., one association between two or more airways), it is to be appreciated that other embodiments may create chains that are greater than one level deep. For example, where airway X is associated with airways Y and Z, subsequent images may detect airways within Y, labelled Y' and Y", that meet the overlap threshold. In those cases, the system may then create a relationship between Y and Y',Y", such as an association chain that includes X→Y→Y',Y".

E.3. Adjusting the Overlap Threshold

FIG. 25 illustrates three examples in which incorrect associations may be determined due to an incorrect setting of the overlap ratio threshold. For example, the relationship shown in images 2500(a) should be two one-to-one associations (e.g., A→A and B→B). However, the overlap illustrated in the fourth column of images 2500(a) may cause airway B of the current image to be associated with airway A of the previous image (or airways A,B to be associated with airways A,B of the previous image). In such a case, the overlap threshold value may be adjusted so that the overlap illustrated in the fourth column of images 2500(a) does not satisfy the overlap condition. Similarly images 2500(b) and 2500(c) illustrate other examples in which incorrect associations may be determined and how the overlap threshold value can be adjusted to prevent such associations (e.g., adjusted such that the overlap illustrated in the fourth column does not satisfy the overlap threshold).

In some embodiments, the overlap ratio threshold can be a design-time parameter configured by the designers of the system. However, in other embodiments, the system may track and record surgical data to track the failure rate of different overlap threshold values. Such systems may utilize such surgical data to train the system on the use of different overlap threshold values and update the system with an updated overlap threshold value that may lead to fewer failure rates. Furthermore, multiple systems may share the surgical data to increase the surgical data available for such training and selection of overlap threshold values.

E.4. Airway Merging Based on Temporal and Spatial Analysis

In Airway Merging, the system may merge two or more current airways based on the determined airway association(s) and data from preoperative model data. To determine whether to merge two or more airways in the current image, the system may determine the current location of the instrument and then determine the number of airways expected at the location from the preoperative model. It is to be appreciated that the system can utilize any number of approaches for determining a location of the instrument. As way of example and not limitation, such approaches may include the sensor fusion system described above, which may include one or more of the following sensor types: EM, vision, robot data, shape sensing fiber, and the like.

The preoperative model data may be stored in a form that allows for retrieval of expected airways for a given location. Such data may be generated before the procedure, where expected airways are indexed by the location of the instrument with respect to the preoperative model. As used here, location may be a positional location with or without orientation, a segment with or without an insertion depth within the segment, or any other representation of location.

Once the system determines that a set of airways in the current image are to be merged, the system may determine the new airway center of the merged airway. The new airway centers can then be used in the image based airway mapping methods described above.

In the example of merging two airways having a single parent airway, the airway centers of the two airways, respectively, can be denoted as $\{x_1, y_1\}$ and $\{x_2, y_2\}$. According to one approach, the airway center of the merged airway may be calculated as a center of the respective center locations of the airways detected in the current image (e.g., geometric shapes representative of the airways in the current image). For example, such a value may be calculated as follows:

$$\{x, y\} = \left\{ \frac{x_1 + x_2}{2}, \frac{y_1 + y_2}{2} \right\} \qquad (5)$$

In another example, the airway center of the merged airway may be calculated as a weighted center of the respective center locations of the airways detected in the current image (e.g., geometric shapes representative of the airways in the current image). For example, such a value may be calculated as follows:

$$\{x, y\} = \left\{ \frac{x_1 \cdot \Lambda_2 + x_2 \cdot \Lambda_1}{\Lambda_1 + \Lambda_2}, \frac{y_1 \cdot \Lambda_2 + y_2 \cdot \Lambda_1}{\Lambda_1 + \Lambda_2} \right\} \qquad (6)$$

where $\Lambda_1$ and $\Lambda_2$ are the areas (e.g., in pixels) of the two airways that are being merged, respectively.

In yet another example, the airway center of the merged airway can be calculated as a center of a bounding polygon that encapsulates the airways detected in the current image (e.g., geometric shapes representative of the airways in the current image). For example, if the coordinates of the left-top corner and right-bottom corner of the rectangle that encapsulates the first one of the two airways are denoted as $\{x_1^{LT}, y_1^{LT}\}$ and $\{x_1^{RB}, y_1^{RB}\}$, and the coordinates of the left-top corner and right-bottom corner of the rectangle that encapsulates the second one of the two airways are denoted as $\{x_2^{LT}, y_2^{LT}\}$ and $\{x_2^{RB}, y_2^{RB}\}$, the corners $\{x^{LT}, y^{LT}\}$ and $\{x^{RB}, y^{RB}\}$ of the encapsulation rectangle can be derived as follows:

$$x^{LT} = \min(x_1^{LT}, x_2^{LT}) \quad (7)$$

$$y^{LT} = \min(y_1^{LT}, y_2^{LT}) \quad (8)$$

$$x^{RB} = \max(x_1^{RB}, x_2^{RB}) \quad (9)$$

$$y^{RB} = \max(y_1^{RB}, y_2^{RB}) \quad (10)$$

Using these values, the airway center of the merged airway can be calculated as the center of the encapsulation rectangle, which is obtained as follows:

$$\{x, y\} = \left\{\frac{x^{LT} + x^{RB}}{2}, \frac{y^{LT} + y^{RB}}{2}\right\} \quad (11)$$

For example, the calculated merged center may be different from any other center location of the airways detected in the current image. As shown in the image 2200(*b*) of FIG. 22, a graphical representation of the merged center of the merged airway may be output on a display of the system instead of the centers of the airways that were merged into the merged airway. In some cases, the merged center may be output on the display along with the centers of the airways that were merged. Although the example techniques of calculating the airway center of the merged airways are described above, other techniques of calculating the airway center representative of the merged airways can be used.

F. Example Image-Based Airway Analysis and Mapping Methods and Systems

Figure 26:
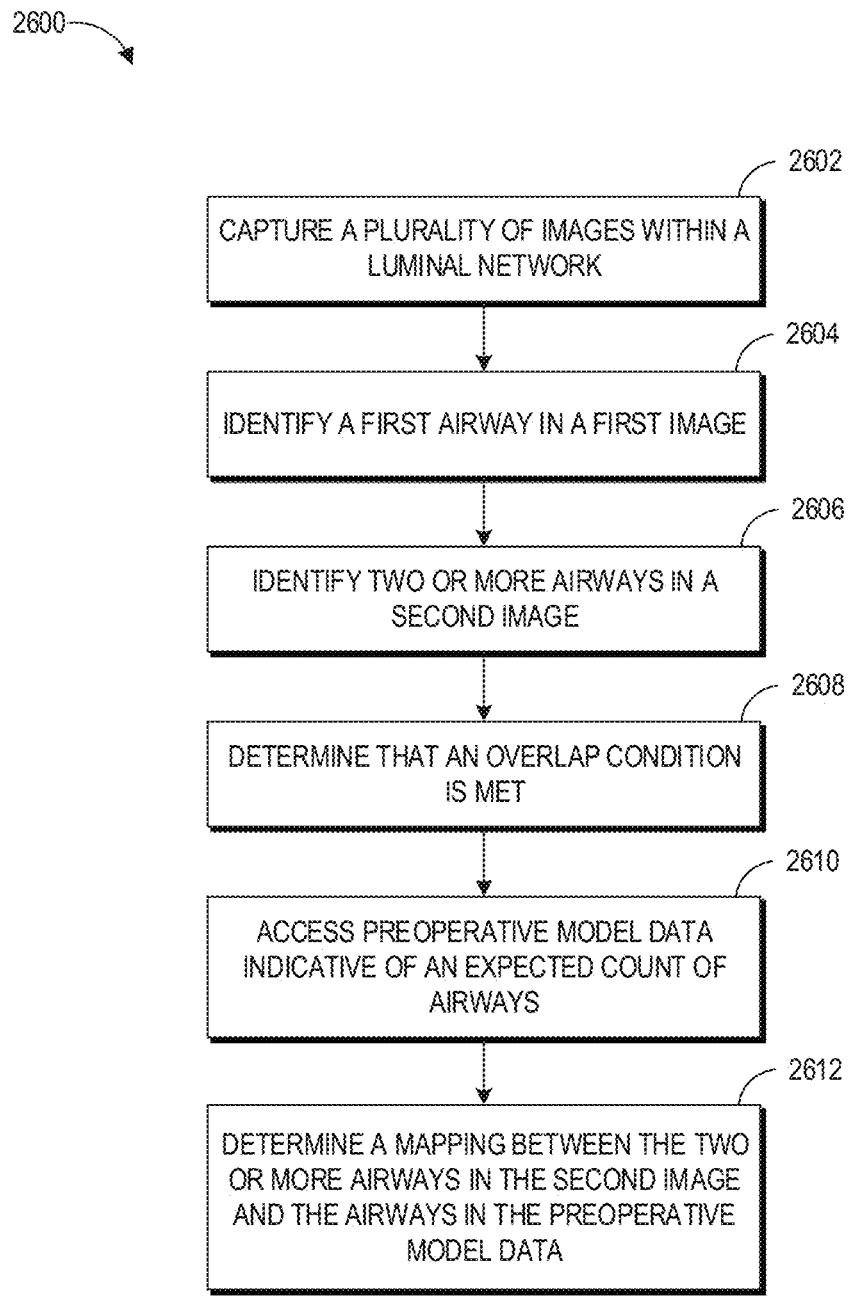
FIG. 26 depicts a flowchart illustrating an example method for image-based airway analysis and mapping.

FIG. 26 illustrates an example method 2600 for implementing the image-based airway analysis and mapping as described above. The method 2600 can be implemented in various of the robotically-controlled systems described throughout this disclosure. The method 2600 can be implemented with a robotic system including an instrument having an elongate body configured to be inserted into a luminal network. An imaging device can be positioned on the elongate body (e.g., on a distal end of the elongate body). The instrument can be attached to an instrument positioning device (e.g., a robotic arm) configured to move the instrument through the luminal network. A system employing the method 2600 can include a processor configured with instructions that cause a processor to execute the method 2600. The method 2600 is provided by way of example only and the image-based airway analysis and mapping can be implemented using different steps than those shown in FIG. 26. For simplicity, the steps illustrated in FIG. 26 are described as being performed by a system (e.g., one of the systems described herein or a system configured to perform one or more of the techniques described here).

At block 2602, the system for mapping one or more airways in a luminal network captures a plurality of images within the luminal network with an imaging device positioned on an instrument. The plurality of images may comprise at least two images, where one of the images (e.g., current image, or second image) is captured at a time subsequent to the other image (e.g., previous image, or first image). The time at which the first image is captured may be referred to as a first time, and the time at which the second image is captured may be referred to as a second time.

At block 2604, the system identifies one or more airways in the first image. In some embodiments, the system identifies a single airway in the first image. In other embodiments, the system identifies multiple airways in the first image. The system may utilize any of the airway identification or detection techniques described herein (e.g., pixel intensity analysis) or other techniques. For example, the identified airways may include one or more polygons or other geometrical shapes whose pixels satisfy the pixel intensity threshold specified by the airway detection method. In some embodiments, a point location such as a centroid is determined and associated with the detected airway.

At block 2606, the system the system identifies two or more airways in the second image. In some embodiments, the system identifies a single airway in the second image. In other embodiments, the system identifies multiple airways in the second image. The system may identify the one or more airways in the second image in a manner similar to that utilized at block 2604.

At block 2608, the system determines, based on the first airway in the first image and the two or more airways in the second image, that an overlap condition is met. The determination that the overlap condition is met may involve, for example: determining a degree of spatial overlap between a first set of one or more geometric shapes representative of the first airway in the first image and a second set of one or more geometric shapes representative of the two or more airways in the second image; and determining the degree of spatial overlap meets or exceeds a defined overlap threshold value, parameter, or indicia. It is to be appreciated that blocks 2602-2606 may involve one or more features described with respect to Airway Tracking and Airway Association. That is, the system may track the location and sizes of airways in a current image as well as the expected locations and sizes of airways previously detected in prior images. When an overlap condition is met, the system may create an association with airways in a prior image and one or more images in a current image. Other associations, as explained above, may be one-to-one or many-to-one.

At block 2610, the system accesses preoperative model data indicative of an expected count of airways corresponding to a location of the instrument during the second time. For example, although not illustrated in FIG. 26, the system may access a position state estimate for the instrument positioned within the luminal network. The position state estimate can include an identification of which branch the instrument is currently positioned (e.g., in the hierarchical structure of luminal network 1000 of FIG. 21). Based on the position state estimate and the preoperative model data (e.g., CT images), the system may determine the expected count of airways corresponding to the location of the instrument during the second time (i.e. at the time the second image is captured). The position state estimate can be determined, for example, by the navigation and localization system 90 of FIG. 15. The position state estimate can be determined based on various and/or multiple position sensing modalities and information, such as preoperative model data 91, vision data 92, EM data 93 (or other position sensing data), and/or robotic command and kinematics data 94.

At block 2612, the system determines, based on the preoperative model data and the determination that the overlap condition is met, a mapping between the two or more airways in the second image and the airways in the preoperative model data. At this block, the system may determine the mapping between airways in the second image and the airways in the preoperative model data using Airway Merging (see section E.4). That is, according to some embodiments, the system may use the data derived from blocks 2602-2606 (Airway Tracking and Airway Association) and a count of the expected number of airways for the current location within the luminal network, as may be determined by preoperative model data, to determine whether or not to merge airways detected in the second image. The system may then map the merged or non-merged to airways in the preoperative model. Mapping airways to preoperative model data is further described in U.S. patent application Ser. No. 15/783,903, filed on Oct. 13, 2017, the entirety of which is incorporated herein by reference and appended hereto as Appendix A.

As just discussed, as part of block 2612, the system may determine the mapping between the two or more airways in the second image and the airways in the preoperative model data based on the preoperative model by accessing the preoperative model data indicative of an expected count of airways corresponding to a location of the instrument during the second time. Accessing the preoperative model data to determine expected airway counts is now explained in greater detail. Although not illustrated in FIG. 26, the preoperative model data may include data structures that allow the system to retrieve the number of airways expected for a given location. Further, the system may access a position state estimate for the instrument positioned within the luminal network. The position state estimate can include an identification of which branch the instrument is currently positioned (e.g., in the hierarchical structure of luminal network 1000 of FIG. 21). Based on the position state estimate and the preoperative model data (e.g., data derived from CT images, in one embodiment), the system may determine the expected count of airways corresponding to the location of the instrument during the second time (i.e. at the time the second image is captured) by accessing the aforementioned data structures. The position state estimate can be determined, for example, by the navigation and localization system 90 of FIG. 15. The position state estimate can be determined based on various and/or multiple position sensing modalities and information, such as preoperative model data 91, vision data 92, EM data 93 (or other position sensing data), and/or robotic command and kinematics data 94.

As further examples, the preoperative model data may indicate that the system is expected to detect branches 1004, 1006 of the luminal network 1000. If the system has detected two airways at block 2606, the system may determine that merging is not needed based on the count of the two or more airways detected in the second image being equal to the expected count of airways indicated by the preoperative model data. In such a case, the system may map the two detected airways to the branches 1004, 1006, respectively (e.g., based on the orientation of the image and/or the two airways) shown in FIG. 21. In the example of FIG. 26, based on the determination that the count of the two or more airways identified in the second image is equal to the expected count of airways indicated by the preoperative model data, the system, at block 2612, may determine the mapping such that each one of the two or more airways identified in the second image is mapped to a different one of the airways in the preoperative model data.

In another example, as illustrated in FIG. 22, the preoperative model data may indicate that the system is expected to detect branches 1004, 1006 of the luminal network 1000, but the system may have detected four airways at block 2606 (e.g., branches 1004, 1012, 1014, 1016). In such a case, the system may merge the four airways into two airways (e.g., by merging the detected airways corresponding to the branches 1012, 1014, 1016 into a single airway), and map the merged airway to the branch 1006, and the unmerged airway to the branch 1004. In the example of FIG. 26, based on the determination that the count of the two or more airways identified in the second image is different than the expected count of airways indicated by the preoperative model data, the system, at block 2612, may determine the mapping such that at least two of the two or more airways identified in the second image is mapped to a single airway in the preoperative model data. In some embodiments, mapping comprises storing the association between the two or more airways in a database. For example, the system may store an indication that a given airway identified in the image branches into two or more airways indicated by the preoperative model data.

As discussed above, the system may confirm, based on the mapping between the two or more airways in the second image and the airways in the preoperative model data, a segment of the luminal network that the instrument is currently located. In some embodiments, the system may adjust, based on the mapping between the two or more airways in the second image and the airways in the preoperative model data, a confidence value of a position state estimate based on other data. For example, this other data may include EM data, robotic data, optical shape sensor data, and inertial measurement unit (IMU) data, any other input data described herein (e.g., input data 91-94 of FIG. 15), or any combination thereof. Additionally or alternatively, the system may predict, based on the mapping between the two or more airways in the second image and the airways in the preoperative model data, a segment of the luminal network that the instrument will be entering.

In one embodiment of block 2608, upon determining that a combination of airways in the current image overlaps with a combination of airways in the previous image by more than a threshold amount (or equal to the threshold amount), the system may merge the combination of airways in the current image into one or more airways such that the number of airways in the current image after the merger matches the number of airways in the combination of airways in the previous image. For example, the system may compare an overlap ratio value (e.g., any of the overlap ratio values in Equations (1)-(3) above) to a threshold overlap value to determine whether an association between the two combinations of airways exists.

As discussed above, the system may also determine the merged center of the merged airway. For example, the system may calculate a merged center location of the combination of airways in the current image (e.g., the set of geometric shapes representative of the combination of airways in the current image), where the merged center location is different than any of respective center locations of the airways detected in the current image (e.g., the geometric shapes in the set that are representative of the combination of airways in the current image).

In the case that the system determines that multiple pairings of combinations of airways satisfy the overlap condition (e.g., A→B having 60% overlap and A→C having 25% overlap), the system may determine the pairing of combinations of airways that has a greater overlap to be in association (e.g., A→B). In some embodiments, the determination of whether an overlap condition is satisfied is not one of degree (e.g., overlap ratio being greater than or equal to a threshold overlap ratio), and is instead a binary determination (e.g., whether the mid-point of three or more segments of a rectangle encapsulating the combination of airways in the current image is within a rectangle encapsulating the combination of airways in the parent image).

In some embodiments, the determination of whether the overlap condition is met may include determining a bounding polygon (e.g., rectangle or other shapes) that encapsulates the combination of airways in the previous image (e.g., the set of geometric shapes representative of the combination of airways in the previous image), determining a bounding polygon that encapsulates the combination of airways in the current image (e.g., the set of geometric shapes representative of the combination of airways in the current image), and determining the degree of spatial overlap based on an overlap between the two bounding polygons.

The image-based airway analysis and mapping techniques described herein compensate the Vision Branch Prediction (VBP) approach or other image-based branch prediction approaches. VBP may not able to perform correct airway mapping in some cases due to the visibility of airways that are from different generations in a given image (e.g., as illustrated in image 2200(*a*) of FIG. 22). The image-based airway analysis and mapping techniques described herein can determine or confirm the hierarchical structure of the airways in a luminal network and determine airway centers that correspond to the same generation. This helps establish correct airway mappings, as illustrated in image 2200(*b*) of FIG. 22).

G. Recursive Distance Searching

In some embodiments, upon determining that two or more airways in the current image are to be merged, the system can merge the airways using recursive distance searching. In doing so, the system may assume that an airway is closer to the airways from its same generation than other generations. For example, this assumption holds true in the example of FIGS. 21 and 22, where the airways in the third generation (e.g., branches 1012, 1014, 1016, illustrated in the bottom right corner in FIG. 22) are all closer to each other than the airway in the second generation (e.g., branch 1004, illustrated in the top left corner in FIG. 22).

In the recursive distance searching may involve a set $P=\{p_i\}_{i=1}^{n}$ which represents a set of n airway centers detected in the current image. Each airway center may be denoted as $p_i=\{x_i, y_i\}$. Then, the system may compute the following value:

$$\{p_i, p_j\} = \underset{\substack{p_i, p_j \in P \\ i<j}}{\operatorname{argmin}} \|p_i - p_j\| \qquad (12)$$

where $\|\cdot\|$ denotes the L2 norm operator. The above equation finds the pair of centers that have the closest distance to each other among the airways centers in the set P, and the system may assume that these two airways are from the same generation. The system then merges the two airways (e.g., obtains the airway center of the merged airway), for example, based on Equations (5)-(11). The system then removes $p_i$ and $p_j$ from P and add $p_k$ into P and repeats this process (e.g., computation, merger, removal, and addition) until only one airway (or a desired number of airways) remains in P.

IV. Implementing Systems and Terminology

Implementations disclosed herein provide systems, methods and apparatus for image-based airway analysis and mapping for navigation robotically-controlled medical instruments. Various implementations described herein provide for improved navigation of luminal networks.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The position estimation and robotic motion actuation functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A method of navigating an instrument through a luminal network, the method comprising:
   capturing a plurality of images within the luminal network with an imaging device positioned on the instrument, the plurality of images comprising at least a first image captured at a first time and a second image captured at a second time subsequent to the first time;
   identifying two or more airways in the first image;
   identifying a first airway in the second image, wherein the first airway in the second image is different from the two or more airways in the first image;
   determining a degree of spatial overlap between a first set of one or more geometric shapes representative of the two or more airways in the first image and a second set of one or more geometric shapes representative of the first airway in the second image;
   accessing preoperative model data indicative of an expected count of airways corresponding to a location of the instrument during the second time;
   determining, based on the preoperative model data and the degree of spatial overlap, a mapping between the first airway in the second image and an airway in the preoperative model data; and
   causing, based at least in part on the mapping between the first airway in the second image and the airway in the preoperative model data, the instrument to move through the luminal network.

2. The method of claim 1, wherein determining the mapping comprises: determining that a count of airways identified in the second image is different than the expected count of airways indicated by the preoperative model data; and determining, based on the degree of spatial overlap, that the two or more airways merge into the first airway.

3. The method of claim 1, wherein the one or more geometric shapes in the first set are detected based on pixels in the first image satisfying a pixel intensity threshold.

4. The method of claim 1, further comprising:
   determining a first bounding polygon that encapsulates the first set of one or more geometric shapes representative of the two or more airways in the first image; and
   determining a second bounding polygon that encapsulates the second set of one or more geometric shapes representative of the first airway in the second image,
   wherein determining the degree of spatial overlap between the first set of one or more geometric shapes and the second set of one or more geometric shapes is based on an overlap between the first bounding polygon and the second bounding polygon.

5. The method of claim 1, wherein determining the degree of spatial overlap comprises determining that the degree of spatial overlap between the first set of one or more geometric shapes and the second set of one or more geometric shapes is greater than a threshold overlap amount.

6. The method of claim 1, further comprising predicting, based on the mapping between the first airway in the second image and the airway in the preoperative model data, a segment of the luminal network that the instrument will be entering.

7. The method of claim 1, further comprising confirming, based on the mapping between the first airway in the second image and the airway in the preoperative model data, a segment of the luminal network that the instrument is currently located.

8. A non-transitory computer readable storage medium having stored thereon instructions that, when executed, cause a processor of a device to at least:
   capture a plurality of images within a luminal network with an imaging device positioned on an instrument, the plurality of images comprising at least a first image captured at a first time and a second image captured at a second time subsequent to the first time;
   identify two or more airways in the first image;
   identify a first airway in the second image, wherein the first airway in the second image is different from the two or more airways in the first image;
   determine a degree of spatial overlap between a first set of one or more geometric shapes representative of the two or more airways in the first image and a second set of one or more geometric shapes representative of the first airway in the second image;
   access preoperative model data indicative of an expected count of airways corresponding to a location of the instrument during the second time;
   determine, based on the preoperative model data and the degree of spatial overlap, a mapping between the first airway in the second image and an airway in the preoperative model data; and
   cause, based at least in part on the mapping between the first airway in the second image and the airway in the preoperative model data, the instrument to move through the luminal network.

9. The non-transitory computer readable storage medium of claim 8, wherein determining the mapping comprises:
   determining that a count of airways identified in the second image is different than the expected count of airways indicated by the preoperative model data; and
   determining, based on the degree of spatial overlap, that the two or more airways merge into the first airway.

10. The non-transitory computer readable storage medium of claim 8, wherein the one or more geometric shapes in the first set are detected based on pixels in the first image satisfying a pixel intensity threshold.

11. The non-transitory computer readable storage medium of claim 8, wherein the one or more geometric shapes in the first set comprise one or more polygons that at least partially overlap with the two or more airways in the first image, and the one or more geometric shapes in the second set comprise one or more polygons that at least partially overlap with the first airway in the second image.

12. The non-transitory computer readable storage medium of claim 8, wherein the instructions, when executed, further cause the processor to adjust, based on the mapping between the first airway in the second image and the airway in the preoperative model data, a confidence value of a position state estimate based on data selected from the group consisting of electromagnetic (EM) data, robotic data, optical shape sensor data, and inertial measurement unit (IMU) data.

13. The non-transitory computer readable storage medium of claim 8, wherein determining the mapping comprises:
   determining that a count of airways identified in the second image is equal to the expected count of airways indicated by the preoperative model data; and
   determining the mapping such that the first airway identified in the second image is mapped to the airway in the preoperative model data in response to determining that the count of airways identified in the second image is equal to the expected count of airways indicated by the preoperative model data.

14. The non-transitory computer readable storage medium of claim 8, wherein determining the mapping comprises:
- determining that a count of airways identified in the second image is different than the expected count of airways indicated by the preoperative model data; and
- determining the mapping such that at least two airways, the at least two airways including the first airway, identified in the second image are mapped to the airway in the preoperative model data in response to determining that the count of airways identified in the second image is different than the expected count of airways indicated by the preoperative model data.

15. A robotic surgical system for mapping one or more airways in a luminal network, the system comprising:
- an instrument having:
  - an elongate body configured to be inserted into the luminal network, and an imaging device positioned on a distal portion of the elongate body;
- an instrument positioning device attached to the instrument, the instrument positioning device configured to move the instrument through the luminal network;
- at least one computer-readable memory having stored thereon executable instructions; and
- one or more processors in communication with the at least one computer-readable memory and configured to execute the instructions to cause the system to at least:
  - capture a plurality of images within the luminal network with the imaging device positioned on the instrument, the plurality of images comprising at least a
  - first image captured at a first time and a second image captured at a second time subsequent to the first time;
  - identify two or more airways in the first image;
  - identify a first airway in the second image, wherein the first airway in the second image is different from the two or more airways in the first image;
  - determine a degree of spatial overlap between a first set of one or more geometric shapes representative of the two or more airways in the first image and a second set of one or more geometric shapes representative of the first airway in the second image;
  - access preoperative model data indicative of an expected count of airways corresponding to a location of the instrument during the second time;
  - determine, based on the preoperative model data and the degree of overlap, a mapping between the first airway in the second image and an airway in the preoperative model data; and
  - cause, based at least in part on the mapping between the first airway in the second image and the airway in the preoperative model data, the instrument to move through the luminal network.

16. The robotic surgical system of claim 15, wherein the one or more geometric shapes in the first set are detected based on pixels in the first image satisfying a pixel intensity threshold.

17. The robotic surgical system of claim 15, wherein the one or more processors are further configured to:
- determine a first bounding polygon that encapsulates the first set of one or more geometric shapes representative of the two or more airways in the first image; and
- determine a second bounding polygon that encapsulates the second set of one or more geometric shapes representative of the first airway in the second image,
- wherein determining the degree of spatial overlap between the first set of one or more geometric shapes and the second set of one or more geometric shapes is based on an overlap between the first bounding polygon and the second bounding polygon.

18. The robotic surgical system of claim 15, wherein determining the degree of spatial overlap comprises determining that the degree of spatial overlap between the first set of one or more geometric shapes and the second set of one or more geometric shapes is greater than a threshold overlap amount.

19. The robotic surgical system of claim 15, wherein the one or more geometric shapes in the first set comprise one or more polygons that at least partially overlap with the two or more airways in the first image, and the one or more geometric shapes in the second set comprise one or more polygons that at least partially overlap with the first airway in the second image.

20. The robotic surgical system of claim 15, wherein determining the mapping comprises:
- determining that a count of airways identified in the second image is different than the expected count of airways indicated by the preoperative model data; and
- determining the mapping such that at least two airways, the at least two airways including the first airway, identified in the second image are mapped to the airway in the preoperative model data in response to determining that the count of airways identified in the second image is different than the expected count of airways indicated by the preoperative model data.

* * * * *